US011653824B2

(12) United States Patent
Takahashi et al.

(10) Patent No.: US 11,653,824 B2
(45) Date of Patent: May 23, 2023

(54) MEDICAL OBSERVATION SYSTEM AND MEDICAL OBSERVATION DEVICE

(71) Applicant: SONY CORPORATION, Tokyo (JP)

(72) Inventors: Kenji Takahashi, Kanagawa (JP); Yasuaki Takahashi, Kanagawa (JP); Takeshi Miyai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 755 days.

(21) Appl. No.: 16/616,142

(22) PCT Filed: Apr. 16, 2018

(86) PCT No.: PCT/JP2018/015686
§ 371 (c)(1),
(2) Date: Nov. 22, 2019

(87) PCT Pub. No.: WO2018/221041
PCT Pub. Date: Dec. 6, 2018

(65) Prior Publication Data
US 2020/0081235 A1    Mar. 12, 2020

(30) Foreign Application Priority Data
May 30, 2017    (JP) .............................. JP2017-106163

(51) Int. Cl.
*G02B 21/00* (2006.01)
*G02B 21/36* (2006.01)
(Continued)

(52) U.S. Cl.
CPC ........ *A61B 1/045* (2013.01); *A61B 1/000095* (2022.02); *A61B 1/00163* (2013.01);
(Continued)

(58) Field of Classification Search
CPC .......... A61B 1/00009; A61B 1/000095; A61B 1/00163; G02B 21/18; G02B 21/367; G02B 21/361; G02B 21/0012
See application file for complete search history.

(56) References Cited

U.S. PATENT DOCUMENTS

| 2012/0105612 A1 | 5/2012 | Yoshino | |
| 2013/0038689 A1* | 2/2013 | McDowall | ........... H04N 5/2355 348/45 |

(Continued)

FOREIGN PATENT DOCUMENTS

| CN | 104812289 A | 7/2015 |
| EP | 2904961 A1 | 8/2015 |

(Continued)

OTHER PUBLICATIONS

International Search Report and Written Opinion of PCT Application No. PCT/JP2018/015686, dated Jul. 10, 2018, 09 pages of ISRWO.

*Primary Examiner* — Mainul Hasan
(74) *Attorney, Agent, or Firm* — Chip Law Group

(57) ABSTRACT

Provided is a medical observation system including a medical observation device and an image processing device. The medical observation device includes a plurality of imaging elements and a branching optical system configured to split incident light into a plurality of rays of light, and each of the plurality of rays of light split by the branching optical system is guided to at least one of the plurality of imaging elements. Of the plurality of imaging elements, two or more imaging elements each capture images having mutually different brightness, and two or more imaging elements are arranged so as to have mutually different optical distances from the branching optical system. The image processing device generates at least one of a first composite image based on a plurality of images having mutually different brightness, the (Continued)

first composite image having a wider dynamic range than each of the plurality of images, or a second composite image based on a plurality of images captured by each of the two or more imaging elements having different optical distances from the branching optical system, the second composite image having a deeper depth of field than each of the plurality of images.

17 Claims, 10 Drawing Sheets

(51) Int. Cl.
    *A61B 1/00*           (2006.01)
    *A61B 1/06*           (2006.01)
    *G02B 21/18*          (2006.01)
    *A61B 1/045*          (2006.01)
    *A61B 1/05*           (2006.01)
(52) U.S. Cl.
    CPC ...... *A61B 1/00188* (2013.01); *G02B 21/0012* (2013.01); *G02B 21/18* (2013.01); *G02B 21/361* (2013.01); *A61B 1/051* (2013.01)

(56) References Cited

U.S. PATENT DOCUMENTS

| | | | |
|---|---|---|---|
| 2013/0041221 A1* | 2/2013 | McDowall | A61B 1/00193 348/E9.037 |
| 2015/0182118 A1* | 7/2015 | Bradbury | A61B 1/045 600/431 |
| 2015/0309284 A1* | 10/2015 | Kagawa | G02B 23/2423 348/76 |
| 2017/0171476 A1* | 6/2017 | Katzir | G02B 26/001 |
| 2019/0113739 A1* | 4/2019 | Homma | G02B 23/2484 |
| 2019/0357757 A1* | 11/2019 | Fengler | A61B 1/043 |
| 2020/0029023 A1* | 1/2020 | Wippermann | H04N 5/23296 |

FOREIGN PATENT DOCUMENTS

| | | |
|---|---|---|
| JP | 2012-095828 A | 5/2012 |
| JP | 2013-128723 A | 7/2013 |
| WO | 2013/061819 A1 | 5/2013 |
| WO | 2014/171284 A1 | 10/2014 |

* cited by examiner

MEDICAL OBSERVATION SYSTEM AND MEDICAL OBSERVATION DEVICE

CROSS REFERENCE TO RELATED APPLICATIONS

This application is a U.S. National Phase of International Patent Application No. PCT/JP2018/015686 filed on Apr. 16, 2018, which claims priority benefit of Japanese Patent Application No. JP 2017-106163 filed in the Japan Patent Office on May 30, 2017. Each of the above-referenced applications is hereby incorporated herein by reference in its entirety.

TECHNICAL FIELD

The present disclosure relates to a medical observation system and a medical observation device.

BACKGROUND ART

Imaging devices are widely used such as digital still cameras and digital video cameras (hereinafter collectively referred to as "digital cameras") including imaging elements such as charge coupled devices (CCDs) and complementary metal oxide semiconductor (CMOS) image sensors. In particular, in recent years, such imaging devices have been also applied to medical observation devices such as endoscopes and surgical microscopes.

Moreover, various types of technology are proposed which enable acquisition of an image, having higher quality than images captured by an imaging device such as a digital camera, on the basis of the above images, and such technology includes the high dynamic range (HDR) or the extended depth of field (EDoF). For example, Patent Document 1 discloses an example of technology for generating a composite image having a deeper depth of field than that of each of multiple images on the basis of the multiple images having different focal distances with respect to a subject.

CITATION LIST

Patent Document

Patent Document 1: International Publication No. 2013-061819

SUMMARY OF THE INVENTION

Problems to be Solved by the Invention

In particular, in recent years, various types of imaging elements capable of capturing images having higher resolution have been proposed along with the increase in resolution of imaging elements. Therefore, there is a demand for technology that enables acquisition of a high quality image in a more preferable manner when such an imaging element is used.

Thus, the present disclosure proposes a medical observation system and a medical observation device that enables acquisition of a high quality image in a more preferable manner.

Solutions to Problems

According to the present disclosure, provided is a medical observation system including: a medical observation device; and an image processing device configured to perform image processing on an image captured by the medical observation device, in which the medical observation device includes a plurality of imaging elements and a branching optical system configured to split incident light into a plurality of rays of light, each of the plurality of rays of light split by the branching optical system is guided to at least one of the plurality of imaging elements, of the plurality of imaging elements, two or more imaging elements each capture images having mutually different brightness, and two or more imaging elements are arranged so as to have mutually different optical distances from the branching optical system, and the image processing device generates at least one of a first composite image based on a plurality of images having mutually different brightness, the first composite image having a wider dynamic range than each of the plurality of images, or a second composite image based on a plurality of images captured by each of the two or more imaging elements having different optical distances from the branching optical system, the second composite image having a deeper depth of field than each of the plurality of images.

According to the present disclosure, also provided is a medical observation device including: a plurality of imaging elements; and a branching optical system configured to split incident light into a plurality of rays of light, in which each of the plurality of rays of light split by the branching optical system is guided to at least one of the plurality of imaging elements, and of the plurality of imaging elements, two or more imaging elements capture images having mutually different brightness, and two or more imaging elements have different optical distances from the branching optical system.

Effects of the Invention

As described above, according to the present disclosure, there are provided a medical observation system and a medical observation device that enables acquisition of a high quality image in a more preferable manner.

Note that the above effects are not necessarily limiting, and any one of effects described herein or other effects that can be grasped from this specification may be exerted together with the above effects or in place of the above effects.

MODE FOR CARRYING OUT THE INVENTION

Preferred embodiments of the present disclosure will be described in detail below with reference to the accompanying drawings. Note that in the present specification and the drawings, components having substantially the same functional configuration are denoted by the same symbol, thereby omitting redundant explanations.

Note that explanation will be given in the following order.
1. Exemplary Configuration of Imaging System
2. Examination on Mechanism Enabling Acquisition of High Quality Images
3. Technical Features
3.1. Exemplary Configuration of Imaging Device
3.2. Functional Configuration
3.3. Variations
4. Exemplary Hardware Configuration
5. Application Examples
6. Conclusion 1. Exemplary Configuration of Imaging System First referring to FIG. 1 and FIG. 2, as an exemplary schematic configuration of an imaging system according to an embodiment of the present disclosure, an example will be described in which the imaging system is configured as a so-called "medical observation system" such as an endoscope imaging system.

Figure 1:
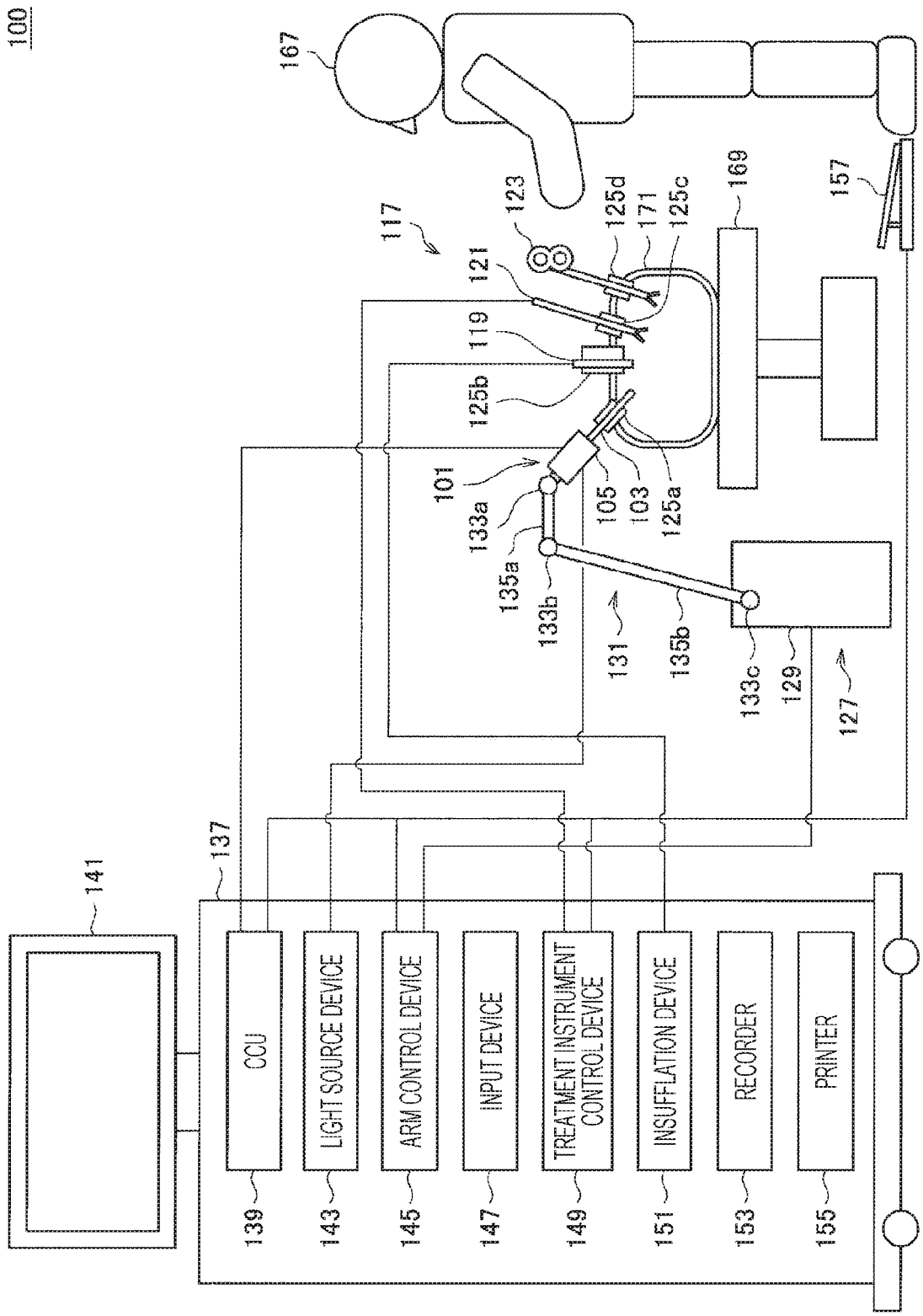
FIG. 1 is a diagram illustrating an exemplary schematic configuration of an endoscope imaging system to which the technology according to the present disclosure is applicable.

For example, FIG. 1 is a diagram illustrating an exemplary schematic configuration of an endoscope imaging system to which the technology according to the present disclosure can be applied, illustrating an exemplary case in which the endoscope imaging system is configured as a so-called endoscopic surgery system. In FIG. 1, a situation is illustrated in which an operator (surgeon) 167 is conducting an operation on a patient 171 on a patient bed 169 using an endoscopic surgery system 100. As illustrated, the endoscopic surgery system 100 includes an endoscope 101, other surgical instruments 117, a support arm device 127 for supporting the endoscope 101, and a cart 137 mounted with various devices for endoscopic surgery.

In endoscopic surgery, instead of cutting and opening the abdominal wall, the abdominal wall is punctured by a plurality of cylindrical drilling instruments called trocars 125a to 125d. Then, a lens barrel 103 of the endoscope 101 and the other surgical instruments 117 are inserted into the body cavity of the patient 171 from the trocars 125a to 125d. In the illustrated example, an insufflation tube 119, an energy treatment instrument 121, and forceps 123 are inserted into the body cavity of the patient 171 as the other surgical instruments 117. Incidentally, the energy treatment instrument 121 is a treatment instrument that performs incision and peeling of tissue, sealing of a blood vessel, and the like by a high-frequency current or ultrasonic vibrations. However, the illustrated surgical instruments 117 are merely an example, and various surgical instruments generally used in endoscopic surgery such as surgical tweezers and retractors may be used as the surgical instruments 117.

An image of an operation site in the body cavity of the patient 171 captured by the endoscope 101 is displayed on a display device 141. The operator 167 performs treatment such as resection of an affected part using the energy treatment instrument 121 or the forceps 123 while viewing the image of the operation site displayed on the display device 141 in real time. Note that, although illustration is omitted, the insufflation tube 119, the energy treatment instrument 121, and the forceps 123 are supported by the operator 167, an assistant, or the like during the operation.

Support Arm Device

The support arm device 127 includes an arm 131 extending from a base 129. In the illustrated example, the arm 131 includes joints 133a, 133b, and 133c, and links 135a and 135b, and is driven by control from an arm control device 145. The endoscope 101 is supported by the arm 131, and the position and the attitude thereof are controlled. In this manner, the endoscope 101 can be secured at a stable position.

Endoscope

The endoscope 101 includes the lens barrel 103 inserted into the body cavity of the patient 171 at a region extending from the tip to a predetermined length, and a camera head 105 connected to a base end of the lens barrel 103. In the illustrated example, the endoscope 101 configured as a so-called rigid endoscope including a rigid lens barrel 103 is illustrated; however, the endoscope 101 may be configured as a so-called flexible endoscope including a flexible lens barrel 103. Note that the camera head 105 or the endoscope 101 including the camera head 105 corresponds to an example of the "medical observation device".

An opening into which an objective lens is fitted is formed at the tip of the lens barrel 103. A light source device 143 is connected to the endoscope 101, and light generated by the light source device 143 is guided to the tip of the lens barrel by a light guide provided in an extending manner inside the lens barrel 103, and emitted toward an observation target (in other words, an imaging object) in the body cavity of the patient 171 via the objective lens. Note that the endoscope 101 may be a forward-viewing endoscope, an oblique-viewing endoscope, or a side-viewing endoscope.

An optical system and an imaging element are provided inside the camera head 105, and reflection light (observation light) from the observation target is condensed on the imaging element by the optical system. The observation light is photoelectrically converted by the imaging element, and an electric signal corresponding to the observation light, that is, an image signal corresponding to an observed image is generated. The image signal is transmitted to a camera control unit (CCU) 139 as raw data. Note that the camera head 105 is mounted with a function of adjusting the magnification and the focal distance by driving the optical system appropriately.

Note that a plurality of imaging elements may be provided to the camera head 105 in order to support, for example, stereoscopic vision (3D display), or the like. In this case, a plurality of relay optical systems is included inside the lens barrel 103 in order to guide observation light to each of the multiple imaging elements.

Various Devices Mounted to Cart

The CCU 139 includes a central processing unit (CPU), a graphics processing unit (GPU), and the like and integrally controls the operation of the endoscope 101 and the display device 141. Specifically, the CCU 139 performs, on the image signal received from the camera head 105, various types of image processing for displaying an image based on the image signal such as development processing (demosaic processing). The CCU 139 provides the image signal applied with the image processing to the display device 141. The CCU 139 also transmits a control signal to the camera head 105 to control driving thereof. The control signal may include information regarding imaging conditions such as the magnification and the focal distance.

The display device 141 displays, under the control by the CCU 139, an image based on the image signal having been applied with the image processing by the CCU 139. In a case where the endoscope 101 supports high-resolution imaging such as 4K (horizontal pixel number 3840×vertical pixel number 2160) or 8K (horizontal pixel number 7680×vertical pixel number 4320), and/or supports 3D display, the display device 141 may be a display device capable of high-resolution display and/or 3D display. In the case of a display device supporting high-resolution imaging such as 4K or 8K, a further sense of immersion can be obtained by using a display device 141 of a size of 55 inches or larger. Furthermore, a plurality of display devices 141 having different resolutions and sizes depending on the application may be provided.

The light source device 143 includes a light source such as a light emitting diode (LED), and supplies the endoscope 101 with illumination light for capturing an operation site.

The arm control device 145 includes a processor such as a CPU, and controls driving of the arm 131 of the support arm device 127 in accordance with a predetermined control method by operating in accordance with a predetermined program.

An input device 147 is an input interface for the endoscopic surgery system 100. A user can input various types of information or instructions to the endoscopic surgery system 100 via the input device 147. For example, the user inputs various types of information regarding an operation such as physical information of a patient and information of an operation procedure via the input device 147. The user further inputs, for example, an instruction to drive the arm 131, an instruction to change the imaging conditions (i.e. type of illumination light, magnification, focal distance, etc.) by the endoscope 101, an instruction to drive the energy treatment instrument 121, etc. via the input device 147.

The type of the input device 147 is not limited, and the input device 147 may be any of various known input devices. For example, a mouse, a keyboard, a touch panel, a switch, a foot switch 157, and/or a lever may be applied as the input device 147. When a touch panel is used as the input device 147, the touch panel may be provided on a display surface of the display device 141.

Alternatively, the input device 147 is a device worn by a user such as a glasses-type wearable device or a head mounted display (HMD), and various types of input are performed depending on the user's gesture or the line-of-sight detected by such device. The input device 147 further includes a camera capable of detecting the user's motion, and various types of input are performed depending on the user's gesture or the line-of-sight detected from a video captured by the camera. Furthermore, the input device 147 includes a microphone capable of picking up the user's voice, and various types of input are performed by the voice via the microphone. In this manner, by configuring the input device 147 to allow various types of information to be input in a non-contact manner, it becomes possible for the user (for example, the operator 167) belonging to a clean area to operate instruments belonging to an unclean area in a non-contact manner. It also becomes possible for a user to operate an instrument without releasing a surgical instrument that the user is holding, and thus the convenience for a user is improved.

A treatment instrument control device 149 controls driving of the energy treatment instrument 121 for cauterization or incision of a tissue, sealing of a blood vessel, and the like. An insufflation device 151 sends gas into a body cavity via the insufflation tube 119 in order to inflate the body cavity of the patient 171 for the purpose of securing a visual field for the endoscope 101 and securing a working space of the operator. A recorder 153 is a device capable of recording various types of information regarding the operation. A printer 155 is a device capable of printing various types of information regarding the operation in various formats such as texts, images or graphs.

Hereinafter, a configuration particularly characteristic to the endoscopic surgery system 100 will be described in more detail.

Support Arm Device

The support arm device 127 includes the base 129 which is a base and an arm 131 extending from the base 129. In the illustrated example, the arm 131 includes the plurality of joints 133a, 133b, and 133c and the plurality of links 135a and 135b coupled by the joint 133b; however in FIG. 1, the structure of the arm 131 is illustrated in a simplified manner. In practice, the shape, the number of, and the arrangement of the joints 133a to 133c and the links 135a and 135b, as well as the direction of the rotation axes of the joints 133a to 133c, or the like may be set as appropriate so that the arm 131 has a desired degree of freedom. For example, the arm 131 may be preferably structured to have more than or equal to six degrees of freedom. This allows the endoscope 101 to freely move within the movable range of the arm 131, thereby allowing the lens barrel 103 of the endoscope 101 to be inserted into the body cavity of the patient 171 from a desired direction.

Actuators are provided to the joints 133a to 133c, thereby allowing the joints 133a to 133c to be rotatable around a predetermined rotation axis by driving of the actuators. The driving of the actuators is controlled by the arm control device 145, whereby the rotation angles of the joints 133a to 133c are controlled, and the driving of the arm 131 is controlled. As a result, control of the position and the attitude of the endoscope 101 can be implemented. At this point, the arm control device 145 can control the driving of the arm 131 by various known control methods such as force control or position control.

For example, the position and the attitude of the endoscope 101 may be controlled when the operator 167 performs operation input as appropriate via the input device 147 (including the foot switch 157) and the driving of the arm 131 is appropriately controlled by the arm control device 145 depending on the operation input. By such control, it is possible to move the endoscope 101 at the tip of the arm 131 from any position to a desired position and to securely support the endoscope 101 at the position after the movement. Note that the arm 131 may be operated by a so-called master/slave scheme. In this case, the arm 131 can be remotely operated by a user via the input device 147 installed at a location distant from the operating room.

Also, in a case where force control is applied, the arm control device 145 may perform so-called power assist control in which the actuators of the joints 133a to 133c are driven so that the arm 131 moves smoothly depending on external force received from a user. As a result, when the user moves the arm 131 while directly touching the arm 131, the arm 131 can be moved by a relatively light force. Therefore, it becomes possible to move the endoscope 101 more intuitively and by simpler operation, and the convenience of the user can be improved.

Here, in endoscopic surgery in general, the endoscope 101 is supported by a surgeon called a scopist. Meanwhile, using the support arm device 127 allows the position of the endoscope 101 to be more reliably secured without manual operation, and thus an image of the operation site can be stably obtained, thereby enabling smooth conduct of the operation.

Note that the arm control device 145 may not necessarily be provided in the cart 137. Moreover, the arm control device 145 may not necessarily be a single device. For example, the arm control device 145 may be provided to each of the joints 133a to 133c of the arm 131 of the support arm device 127, and the drive control of the arm 131 may be implemented by cooperation of the plurality of arm control devices 145.

Light Source Device

The light source device 143 supplies the endoscope 101 with illumination light for capturing an operation site. The light source device 143 includes, for example, a white light source including an LED, a laser light source, or a combination thereof. Here, in a case where the white light source includes a combination of RGB laser light sources, it is possible to adjust the white balance of a captured image in the light source device 143 since the output intensity and the output timing of each color (each wavelength) can be controlled with high accuracy. In this case, it is also possible to capture images corresponding to each of the RGB in time division by emitting laser light from each of the RGB laser light sources toward an observation target in time division and controlling the driving of the imaging element in the camera head 105 in synchronization with the emission timing. According to this method, a color image can be obtained without providing a color filter in the imaging element.

In addition, the driving of the light source device 143 may be controlled so as to change the output intensity of light for every predetermined period of time. By controlling the driving of the imaging element in the camera head 105 in synchronization with the timing of the change of the light intensity to acquire images in time division and by combining these images, it becomes possible to generate a high dynamic range image free from so-called black defects or halation.

In addition, the light source device 143 may be configured to be capable of supplying light of a predetermined wavelength band corresponding to special light observation. In special light observation, for example using the wavelength dependency of light absorption in body tissues, so-called narrow band imaging is performed in which a predetermined tissue such as a blood vessel in the mucous membrane surface layer is captured with high contrast by emitting narrow band light as compared with the illumination light for normal observation (that is, white light). Alternatively, in special light observation, fluorescence observation may be performed in which an image is obtained by fluorescence generated by irradiation with excitation light. Fluorescence observation includes observation in which a body tissue is irradiated with excitation light and fluorescence from the body tissue (autofluorescence observation) is observed, observation in which a reagent such as indocyanine green (ICG) is locally injected into a body tissue and the body tissue is irradiated with excitation light corresponding to the fluorescence wavelength of the reagent to obtain a fluorescence image, and the like. The light source device 143 can be configured to be capable of supplying narrow band light and/or excitation light corresponding to such special light observation.

Camera Head and CCU

Figure 2:
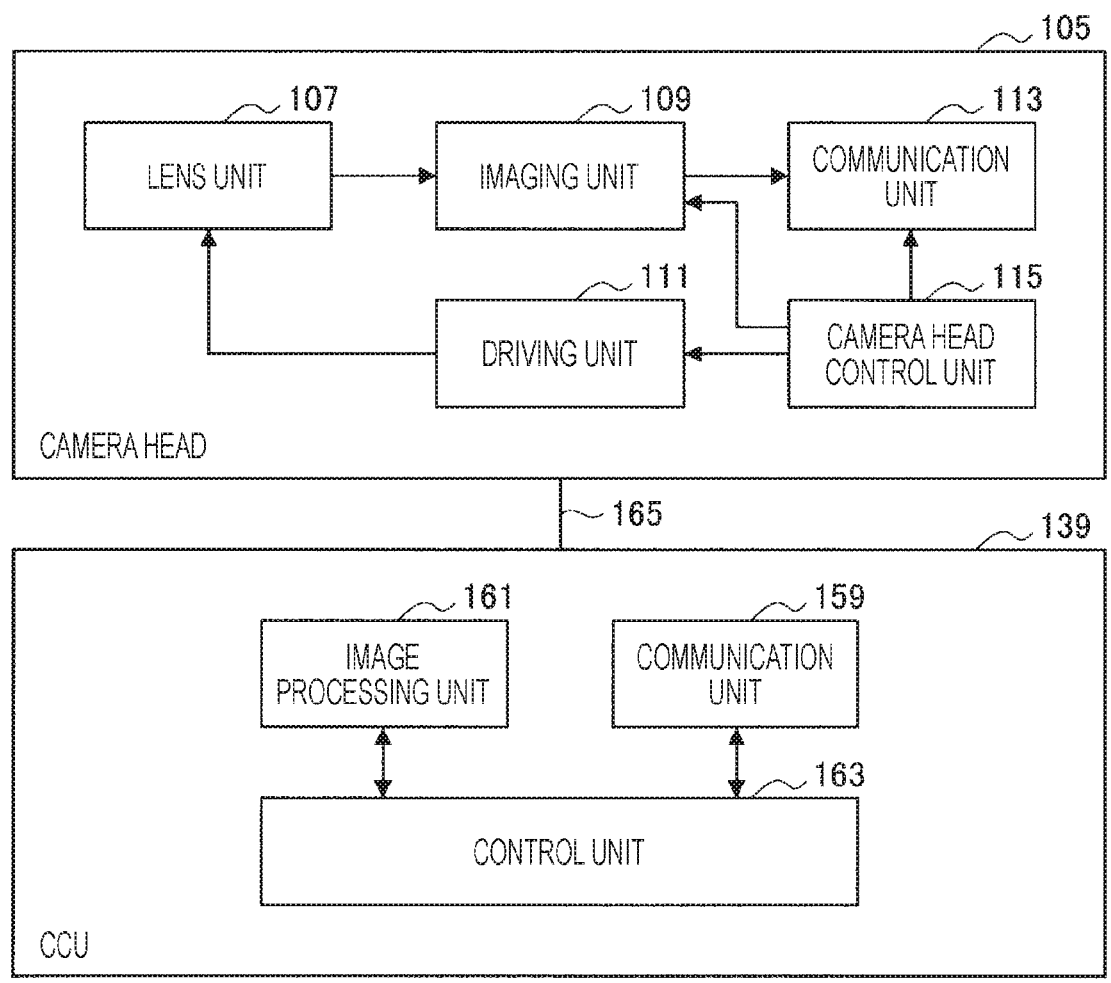
FIG. 2 is a block diagram illustrating an example of functional configurations of a camera head and a CCU illustrated in FIG. 1.

The functions of the camera head 105 and the CCU 139 of the endoscope 101 will be described in more detail with reference to FIG. 2. FIG. 2 is a block diagram illustrating an example of functional configurations of the camera head 105 and the CCU 139 illustrated in FIG. 1.

Referring to FIG. 2, the camera head 105 includes, as its functions, a lens unit 107, an imaging unit 109, a driving unit 111, a communication unit 113, and a camera head control unit 115. Meanwhile, the CCU 139 includes a communication unit 159, an image processing unit 161, and a control unit 163 as its functions. The camera head 105 and the CCU 139 are coupled in a bidirectionally-communicable manner by a transmission cable 165.

First, the functional configuration of the camera head 105 will be described. The lens unit 107 is an optical system provided at a coupling portion with the lens barrel 103. The observation light taken in from the tip of the lens barrel 103 is guided toward the camera head 105 and enters the lens unit 107. The lens unit 107 includes a combination of a plurality of lenses including a zoom lens and a focus lens. The optical characteristics of the lens unit 107 are adjusted so as to condense the observation light on a light receiving surface of the imaging element of the imaging unit 109. Moreover, the position of the zoom lens or the focus lens is movable on the optical axis thereof in order to adjust the magnification and the focus of an image to be captured.

The imaging unit 109 includes the imaging element, and is disposed as a subsequent stage of the lens unit 107. The observation light which has passed through the lens unit 107 is condensed on the light receiving surface of the imaging element, and an image signal corresponding to an observed image is generated by photoelectric conversion. The image signal generated by the imaging unit 109 is provided to the communication unit 113.

As the imaging element included in the imaging unit 109, for example an image sensor of a complementary metal oxide semiconductor (CMOS) type which has a Bayer array and capable of color imaging is used. Note that, as the imaging element, for example an imaging element supporting high resolution imaging of 4K or more may be used. By obtaining an image of the operation site at high resolution, the operator 167 can grasp the situation of the operation site in more detail, thereby enabling smooth progress of the operation.

In addition, the imaging element included in the imaging unit 109 includes a pair of imaging elements for acquiring image signals for the right eye and the left eye to support 3D display. The 3D display enables the operator 167 to more accurately grasp the depth of a biological tissue in the operation site. Note that, in a case where the imaging unit 109 is a multi-plate type, a plurality of lens units 107 is also provided corresponding to each of the imaging elements.

Incidentally, the imaging unit 109 may not necessarily be provided in the camera head 105. For example, the imaging unit 109 may be provided inside the lens barrel 103 immediately after the objective lens.

The driving unit 111 includes an actuator, and moves the zoom lens and the focus lens of the lens unit 107 by a predetermined distance along the optical axis under the control by the camera head control unit 115. As a result, the magnification and the focus of an image to be captured by the imaging unit 109 can be appropriately adjusted.

The communication unit 113 includes a communication device for transmitting and receiving various types of information to and from the CCU 139. The communication unit 113 transmits the image signal obtained from the imaging unit 109 to the CCU 139 via the transmission cable 165 as raw data. At this point, it is preferable that the image signal be transmitted by optical communication in order to display the captured image of the operation site with low latency. This is because it is desired to display moving images of the operation site in real time as much as possible for the sake of safer and more reliable operation since the operator 167 conducts the operation while observing the condition of the affected part by the captured image during the operation. In a case where optical communication is performed, the communication unit 113 includes a photoelectric conversion module that converts an electric signal into an optical signal. The image signal is converted into an optical signal by the photoelectric conversion module, and then transmitted to the CCU 139 via the transmission cable 165.

The communication unit 113 also receives, from the CCU 139, a control signal for controlling the driving of the camera head 105. The control signal includes information regarding imaging conditions such as information designating a frame rate of an image to be captured, information designating an exposure value for imaging, and/or information designating a magnification and focus of an image to be captured. The communication unit 113 provides the received control signal to the camera head control unit 115. Note that the control signal from CCU 139 may also be transmitted by optical communication. In this case, the communication unit 113 includes a photoelectric conversion module that converts an optical signal into an electric signal, and the control signal is converted into an electric signal by the photoelectric conversion module and is then provided to the camera head control unit 115.

Note that the imaging conditions such as the frame rate, the exposure value, the magnification, and the focus mentioned above are automatically set by the control unit 163 of the CCU 139 on the basis of the acquired image signal. That is, a so-called auto exposure (AE) function, an auto focus (AF) function, and an auto white balance (AWB) function are mounted on the endoscope 101.

The camera head control unit 115 controls the driving of the camera head 105 on the basis of the control signal from the CCU 139 having been received via the communication unit 113. For example, the camera head control unit 115 controls driving of the imaging elements of the imaging unit 109 on the basis of the information designating a frame rate of an image to be captured and/or the information designating an exposure for imaging. Moreover, for example, the camera head control unit 115 moves the zoom lens and the focus lens of the lens unit 107 via the driving unit 111 as appropriate on the basis of the information designating a magnification and focus of an image to be captured. The camera head control unit 115 may further have a function of storing information for identifying the lens barrel 103 or the camera head 105.

Note that by disposing components likes the lens unit 107, the imaging unit 109, or the like in a sealed structure having high airtightness and waterproofness, the camera head 105 can be made resistant against autoclave sterilization.

Next, the functional configuration of the CCU 139 will be described. The communication unit 159 includes a communication device for transmitting and receiving various types of information to and from the camera head 105. The communication unit 159 receives an image signal transmitted from the camera head 105 via the transmission cable 165. At this point, as described above, the image signal can be suitably transmitted by optical communication. In this case, the communication unit 159 includes a photoelectric conversion module that converts an optical signal into an electric signal to support optical communication. The communication unit 159 provides the image signal converted into the electrical signal to the image processing unit 161.

The communication unit 159 also transmits a control signal for controlling the driving of the camera head 105 to the camera head 105. This control signal may also be transmitted by optical communication.

The image processing unit 161 performs various types of image processing on the image signal, which is raw data, transmitted from the camera head 105. As the image processing, various types of known signal processing are included such as development processing, image quality improvement processing (for example, band enhancement processing, super-resolution processing, noise reduction (NR) processing, and/or camera shake correction processing), and/or enlargement processing (electronic zoom processing, or the like). The image processing unit 161 also performs detection processing on the image signal to perform AE, AF, and AWB.

The image processing unit 161 includes a processor such as a CPU or a GPU, and the image processing and the detection processing described above can be performed by the processor operating in accordance with a predetermined program. Note that in a case where the image processing unit 161 includes a plurality of GPUs, the image processing unit 161 divides information regarding the image signal as appropriate and performs image processing by the plurality of GPUs in parallel.

The control unit 163 performs various types of control regarding imaging of an operation site by the endoscope 101 and display of the captured image. For example, the control unit 163 generates a control signal for controlling the driving of the camera head 105. At this point, in a case where the imaging conditions are input by a user, the control unit 163 generates the control signal on the basis of the input by the user. Alternatively, in a case where the endoscope 101 is mounted with the AE function, the AF function, and the AWB function, the control unit 163 calculates the optimum exposure value, focal distance, and white balance as appropriate depending on the result of the detection processing by the image processing unit 161 to generate the control signal.

The control unit 163 further causes the display device 141 to display an image of the operation site on the basis of the image signal having been applied with the image processing by the image processing unit 161. At this point, the control unit 163 recognizes various objects in the operation site image using various types of image recognition technology. For example, the control unit 163 can recognize a surgical instrument such as forceps, a specific biological part, bleeding, mist at the time of using the energy treatment instrument 121, etc. by detecting the shape, the color, and the like of an edge of an object included in the operation site image. When displaying the image of the operation site on the display device 141, the control unit 163 superimposes and displays various types of surgery support information over the image of the operation site using the recognition result. The surgery support information superimposed and displayed and thereby presented to the operator 167 enables safer and more reliable progress of the operation.

The transmission cable 165 coupling the camera head 105 and the CCU 139 is an electric signal cable supporting communication of electric signals, an optical fiber supporting optical communication, or a composite cable thereof.

Although communication is performed in a wired manner using the transmission cable 165 in the illustrated example, communication between the camera head 105 and the CCU 139 may be performed wirelessly. Since there is no need to lay the transmission cable 165 in the operating room in a case where communication between the two is performed wirelessly, the situation that the movement of the medical staff in the operating room is hindered by the transmission cable 165 can be eliminated.

An example of the endoscopic surgery system 100 to which the technology according to the present disclosure can be applied has been described above. Note that although the endoscopic surgery system 100 has been described as one example here, a system to which the technology of the present disclosure can be applied is not limited to such example. For example, the technology of the present disclosure may be applied to a flexible endoscopic system for examination or a microsurgery system.

2. Examination on Mechanism Enabling Acquisition of High Quality Images

Various types of technology have been proposed to enable acquisition of an image, having higher quality than images captured by an imaging device such as a digital camera, on the basis of the above images. Specific examples of such technology include technology called the high dynamic range (HDR) or the extended depth of field (EDoF).

HDR is technology for generating an image having a wider dynamic range than each of multiple images by combining the multiple images having different exposure conditions (for example, multiple images having different dynamic ranges). Meanwhile, EDoF is technology for generating an image having a deeper depth of field than each of multiple images (that is, an image having a wider range in a depth direction which is in focus) for example by combining the multiple images having different in-focus distances with respect to a subject.

The technology that enables acquisition of such high quality images is also expected to be introduced into an imaging system as described above with reference to FIGS. 1 and 2, for example.

In particular, in recent years, it has become possible to capture an image having higher resolution with the increase in resolution of imaging elements (that is, with reduced pixel pitches). Meanwhile, there are cases where imaging conditions under which an image having a higher resolution can be obtained by such a high-definition imaging element are limited as compared with an imaging element having a wider pixel pitch. One specific example is that the depth of field of a captured image tends to be shallower since the depth of focus of the image becomes shallower as the resolution of the image becomes higher with the increase in resolution of the imaging element. Such a characteristic tends to be more pronounced, especially at a resolution higher than or equal to 4K.

In view of such a situation, the present disclosure proposes exemplary technology that enables acquisition of a high quality image in a more preferable manner even under a situation where a higher resolution image is captured using high definition imaging elements.

3. Technical Features

The technical features of an imaging device according to the present embodiment will be described below.

3.1. Exemplary Configuration of Imaging Device

Figure 3:
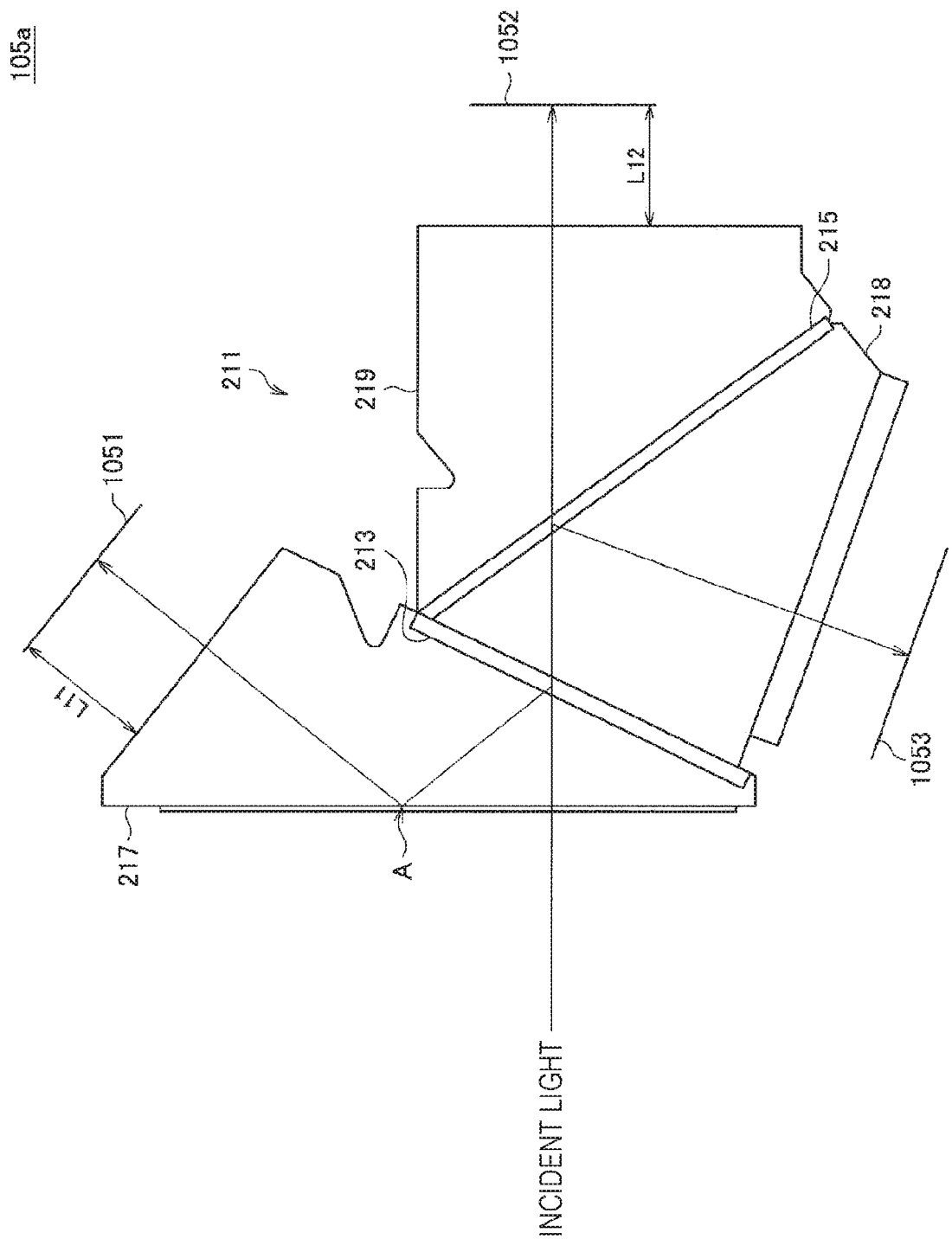
FIG. 3 is an explanatory diagram for explaining an exemplary configuration of an imaging device of an embodiment of the present disclosure.

First with reference to FIG. 3, an exemplary schematic configuration of an imaging device according to the present embodiment will be described focusing on a process for light incident on the imaging device to form an image on an imaging element. FIG. 3 is an explanatory diagram for explaining an exemplary configuration of an imaging device according to the present embodiment and illustrating an exemplary imaging device applicable as the camera head 105 of the endoscopic surgery system 100 described above. Note that, in the following description, the imaging device illustrated in FIG. 3 may be referred to as the "imaging device 105*a*" in order to explicitly distinguish it from other imaging devices applicable as the camera head 105.

As illustrated in FIG. 3, the imaging device 105*a* according to the present embodiment includes a branching optical system 211 and first imaging element 1051 to third imaging element 1053.

In the case of capturing a color image of a subject by the imaging device 105*a*, for example, R pixels, B pixels, and G pixels are arranged in the first imaging element 1051 to third imaging element 1053. In this case, for example, imaging elements having a so-called Bayer array may be applied as the first imaging element 1051 to the third imaging element 1053. Alternatively as another example, in a case where a black and white image of a subject is captured by the imaging device 105*a*, imaging elements not including a color filter may be applied as the first imaging element 1051 to the third imaging element 1053.

Moreover, imaging elements having a valid pixel number that corresponds to the resolution of ultra high-definition (UHD), high-definition (HD), or standard definition (SD), such as 8K and 4K, may be applied as the first imaging element 1051 to the third imaging element 1053. Note that it is more preferable that the first imaging element 1051 to the third imaging element 1053 have a valid pixel number corresponding to a resolution higher than or equal to 4K.

The branching optical system 211 splits the light incident on the imaging device 105*a* (hereinafter also referred to as "incident light") into a plurality of rays of light, and allows each of the split rays of light to form an image on first imaging element 1051 to third imaging element 1053.

Specifically, as illustrated in FIG. 3, the branching optical system 211 is a prism obtained by joining a first prism 217 and a second prism 218 via a beam splitter 213 and joining the second prism 218 and a third prism 219 via a beam splitter 215. That is, the beam splitter 213 is provided at the boundary between the first prism 217 and the second prism 218. Likewise, the beam splitter 215 is provided at the boundary between the second prism 218 and the third prism 219.

The beam splitter 213 splits the incident light into a plurality of rays of light by reflecting a part of the incident light. Note that the ratio between the light reflected by the beam splitter 213 and the light transmitted by the beam splitter 213 is determined depending on the reflectance (in other words, transmittance) of the beam splitter 213. Similarly, the beam splitter 215 splits the light into a plurality of rays of light by reflecting a part of the light transmitted by the beam splitter 213. That is, the ratio between the light reflected by the beam splitter 215 and the light transmitted by the beam splitter 215 is determined depending on the reflectance (in other words, transmittance) of the beam splitter 215. At least one of the beam splitters 213 and 215 may be a so-called semitransparent mirror film.

The first prism 217 is a prism which the incident light on the imaging device 105a enters, and functions as an optical path through which a part of the incident light reflected by the beam splitter 213 is guided. The second prism 218 is a prism which the light transmitted by the beam splitter 213 enters, and functions as an optical path through which a part of the incident light reflected by the beam splitter 215 is guided. The third prism 219 functions as an optical path through which the light transmitted by the beam splitter 215 is guided.

The incident light incident on the first prism 217 travels straight through the first prism 217, and a part thereof is reflected by the beam splitter 213 provided obliquely on the optical axis, and the other part is transmitted by the beam splitter 213, thereby split into a plurality of rays of light.

The light reflected and split by the beam splitter 213 is guided in the first prism 217. Here, the light reflected and split is totally reflected only once at a position A illustrated in FIG. 3 and then is transmitted to the outside of the first prism 217. This allows the angle of the film-formed surface of the beam splitter 213 with respect to the optical axis to be closer to a right angle. Conversely, the installation angle of the beam splitter 213 according to the present embodiment on the optical axis is set in such a manner that the conditions for total reflection of visible light rays at the position A are satisfied. The light transmitted by the first prism 217 is guided to the first imaging element 1051. Note that another optical system may be interposed between the first prism 217 and the first imaging element 1051.

The light transmitted by the beam splitter 213 enters the second prism 218. The light incident on the second prism 218 travels straight through the second prism 218, and a part thereof is reflected by the beam splitter 215 provided obliquely on the optical axis, and the other part is transmitted by the beam splitter 215, thereby split into a plurality of rays of light.

The light reflected and split by the beam splitter 215 is guided in the second prism 218. The end surface of the second prism 218 on the opposite side to the side where the beam splitter 215 is provided (in other words, the exit surface on the downstream side of the optical axis of the second prism 218) is perpendicular to the optical axis. Therefore, the light reflected and split by the beam splitter 215 is transmitted to the outside of the second prism 218 while maintaining the state of being perpendicular to the exit surface of the second prism 218. The light transmitted by the second prism 218 is guided to the third imaging element 1053. Note that another optical system may be interposed between the second prism 218 and the third imaging element 1053.

The light transmitted by the beam splitter 215 enters the third prism 219 and travels straight through the inside of the third prism 219. The end surface of the third prism 219 on the opposite side to the side where the beam splitter 215 is provided (in other words, the exit surface on the downstream side of the optical axis of the third prism 219) is perpendicular to the optical axis. Therefore, the light transmitted by the beam splitter 215 is transmitted to the outside of the third prism 219 while maintaining the state of being perpendicular to the exit surface of the third prism 219. The light transmitted by the third prism 219 is guided to the second imaging element 1052. Note that another optical system may be interposed between the third prism 219 and the second imaging element 1052.

Moreover, the imaging device 105a according to the present embodiment is configured in such a manner that two or more imaging elements out of the first imaging element 1051 to the third imaging element 1053 capture images having mutually different brightness. As one specific example, it is preferable that the imaging device 105a be configured to allow the brightness of images captured by the first imaging element 1051, the second imaging element 1052, and the third imaging element 1053 to be 4:4:1, respectively. With such a configuration, for example by combining the images having mutually different brightness, captured by each of the second imaging element 1052 and the third imaging element 1053, it becomes possible to generate an image having a wider dynamic range than each of the images (for example, high dynamic range (HDR) image).

Note that, as long as images having mutually different brightness are captured by two or more imaging elements, the configuration for capturing the images is not particularly limited. As one specific example, the amount of light for forming an image on each of the first imaging element 1051 to the third imaging element 1053 may be adjusted by adjustment of the reflectance (transmittance) of the beam splitters 213 and 215. As one specific example, the reflectance (transmittance) of the beam splitter 213 may be adjusted so that the difference in the amount of light between the transmission light and the reflection light becomes 5:4. Alternatively, the reflectance (transmittance) of the beam splitter 213 may be adjusted so that the difference in the amount of light between the transmission light and the reflection light becomes 4:1. With such a configuration, the ratio of the amount of light forming an image on each of the first imaging element 1051, the second imaging element 1052, and the third imaging element 1053 becomes 4:4:1.

Alternatively, as another example, the shutter speed of each of two or more of the first imaging element 1051 to third imaging element 1053 may be controlled to allow the two or more imaging elements to capture images having mutually different brightness. Furthermore, as still another example, the sensitivity of each of the two or more imaging elements may be controlled to allow the two or more imaging elements to capture images having mutually different brightness. In addition, as yet another example, a diaphragm may be provided to at least one of the two or more imaging elements as a preceding stage thereof, and the diaphragm may be controlled to control the amount of light for forming an image on each of the two or more imaging elements.

In the imaging device 105a according to the present embodiment, two or more of the first imaging element 1051 to the third imaging element 1053 are arranged so as to have mutually different optical distances from the branching optical system 211. More specifically, the branching optical system 211 is telecentric on both sides, and the two or more imaging elements are arranged in such a manner that the optical distances from exit ends of the branching optical system 211 are different from each other. With such a configuration, the two or more imaging elements capture images having mutually different distances at which a subject is in focus. In other words, it can be said that the two or more imaging elements have mutually different focal distances using the branching optical system 211 as a reference. Note that the "optical distance" corresponds to an optical distance calculated from the traveling speed of light, and is calculated from the physical distance of an optical path and the refractive index in the path.

For example, in FIG. 3, symbol L11 denotes an optical distance between an exit end of the branching optical system 211 (first prism 217) from which light that forms an image on the first imaging element 1051 exits and the first imaging element 1051. In addition, symbol L12 denotes an optical distance between an exit end of the branching optical system 211 (third prism 219) from which light that forms an image on the second imaging element 1052 exits and the second imaging element 1052. That is, in the example illustrated in FIG. 3, the first imaging element 1051 and the second imaging element 1052 may be arranged in such a manner that the optical distance L11 and the optical distance L12 become different from each other.

Figure 4:
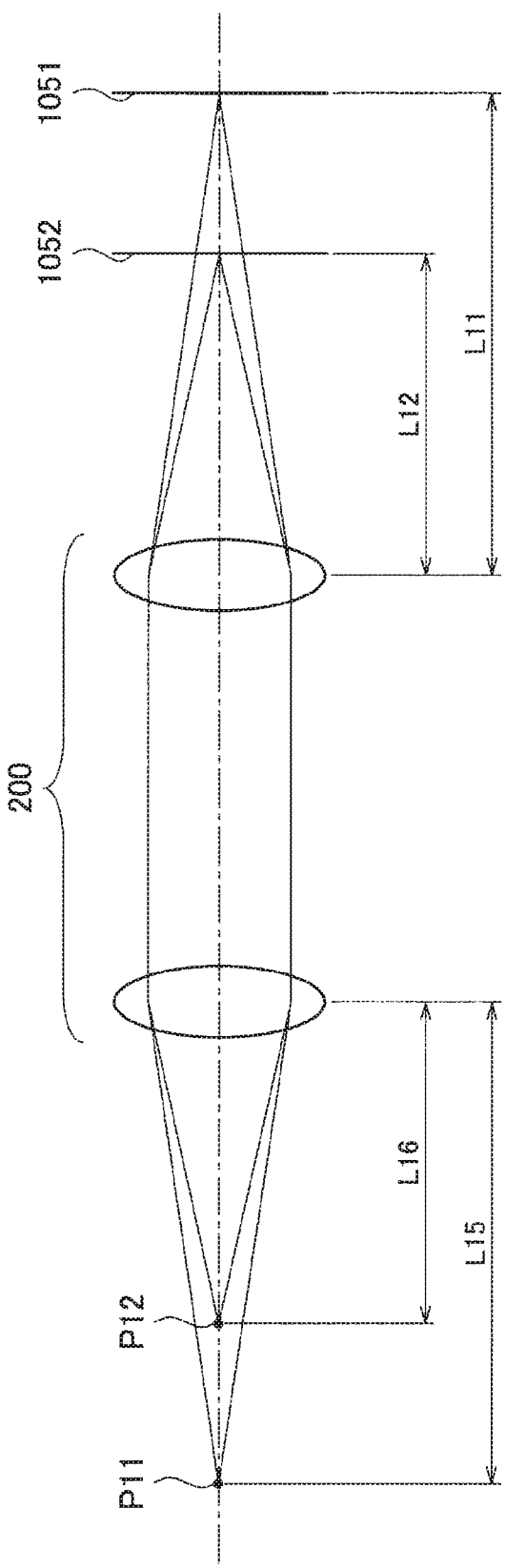
FIG. 4 is an explanatory diagram for explaining an outline of the imaging device of the embodiment.

For example, FIG. 4 is an explanatory diagram for explaining an outline of the imaging device 105a according to the present embodiment. Specifically, FIG. 4 is a diagram schematically illustrating the optical positional relationship among each of the first imaging element 1051 and the second imaging element 1052 and an optical system for guiding light to each of the first imaging element 1051 and the second imaging element 1052 such as the branching optical system 211. In FIG. 4, symbol 200 schematically indicates the optical system for guiding light to each of the first imaging element 1051 and the second imaging element 1052, and may include an optical system (e.g. endoscope, microscope, etc.) such as a lens attached to the imaging device 105a (e.g. camera head) or the branching optical system 211 illustrated in FIG. 3. In addition, the symbols L11 and L12 schematically indicate the optical distances L11 and L12 illustrated in FIG. 3.

As illustrated in FIG. 4, the optical distances L11 and L12 for light after exiting the optical system 200 after being guided by the optical system 200 to form an image on the first imaging element 1051 and the second imaging element 1052, respectively, are different from each other. That is, it can be said that the first imaging element 1051 and the second imaging element 1052 have mutually different focal distances using the optical system 200 as a reference. Therefore, images of a subject having different distances from the optical system 200 (that is, subject distances) are formed on each of the first imaging element 1051 and the second imaging element 1052. In other words, the first imaging element 1051 and the second imaging element 1052 capture images having mutually different distances at which a subject is in focus.

As one specific example, in the example illustrated in FIG. 4, an image of a subject denoted by symbol P12 is formed on the second imaging element 1052. For example, in FIG. 4, symbol L16 schematically indicates the optical distance from the optical system 200 to the subject P12 (in other words, subject distance). On the other hand, the first imaging element 1051 has a longer optical distance from the optical system 200 than the second imaging element 1052. Therefore, an image of a subject indicated by symbol P11, that is, a subject, spaced farther away than the subject P12 is with respect to the optical system 200, is formed on the first imaging element 1051. For example, in FIG. 4, symbol L16 schematically indicates the optical distance from the optical system 200 to the subject P12 (in other words, subject distance).

With such a configuration, for example by combining images captured by each of the second imaging element 1052 and the first imaging element 1051 on which images of subjects having mutually different subject distances are formed, it becomes possible to generate an image having a deeper depth of field (for example, extended depth of field (EDoF) image) than the above images.

Meanwhile, in a case where the imaging device 105a is configured as the camera head 105 of the endoscope 101 as in the example having been described with reference to FIG. 1 and FIG. 2, a subject of concern is more likely to be saturated in the front side than in the far side. In such a case, therefore, for example in the example illustrated in FIG. 4 assuming the subject distance corresponding to the second imaging element 1052 as a reference, it is desirable that the first imaging element 1051 be arranged so as to have a subject distance shorter than that of the second imaging element 1052 (that is, so as to have a shallower focus). That is, in this case, it is desirable that the first imaging element 1051 be arranged so as to have a shorter optical distance from the optical system 200 than that of the second imaging element 1052.

Note that the example of a so-called three-plate imaging device including the three imaging elements has been described above; however, a configuration of an imaging device according to the present embodiment is not necessarily limited thereby. Specifically, the number of imaging elements may be four or more as long as each rays of light split from the incident light by the branching optical system forms an image on each of the multiple imaging elements. Moreover, it is also possible to add another function without limiting to the HDR and the EDoF by adding (an) imaging element(s). As one specific example, by separately adding an imaging element capable of detecting light belonging to an infrared (IR) wavelength band, it also becomes possible to apply the imaging device according to the present embodiment to fluorescence observation using as a phosphor such as indocyanine green (ICG). Furthermore, as another example, by shifting the phase of the Bayer array between multiple imaging elements and combining images captured by each of the multiple imaging devices, it becomes possible to generate an image having a higher resolution than each of the above images.

First with reference to FIG. 3, an exemplary schematic configuration of the imaging device according to the present embodiment has been described above focusing on a process for light incident on the imaging device to form an image on an imaging element.

3.2. Functional Configuration

Figure 5:
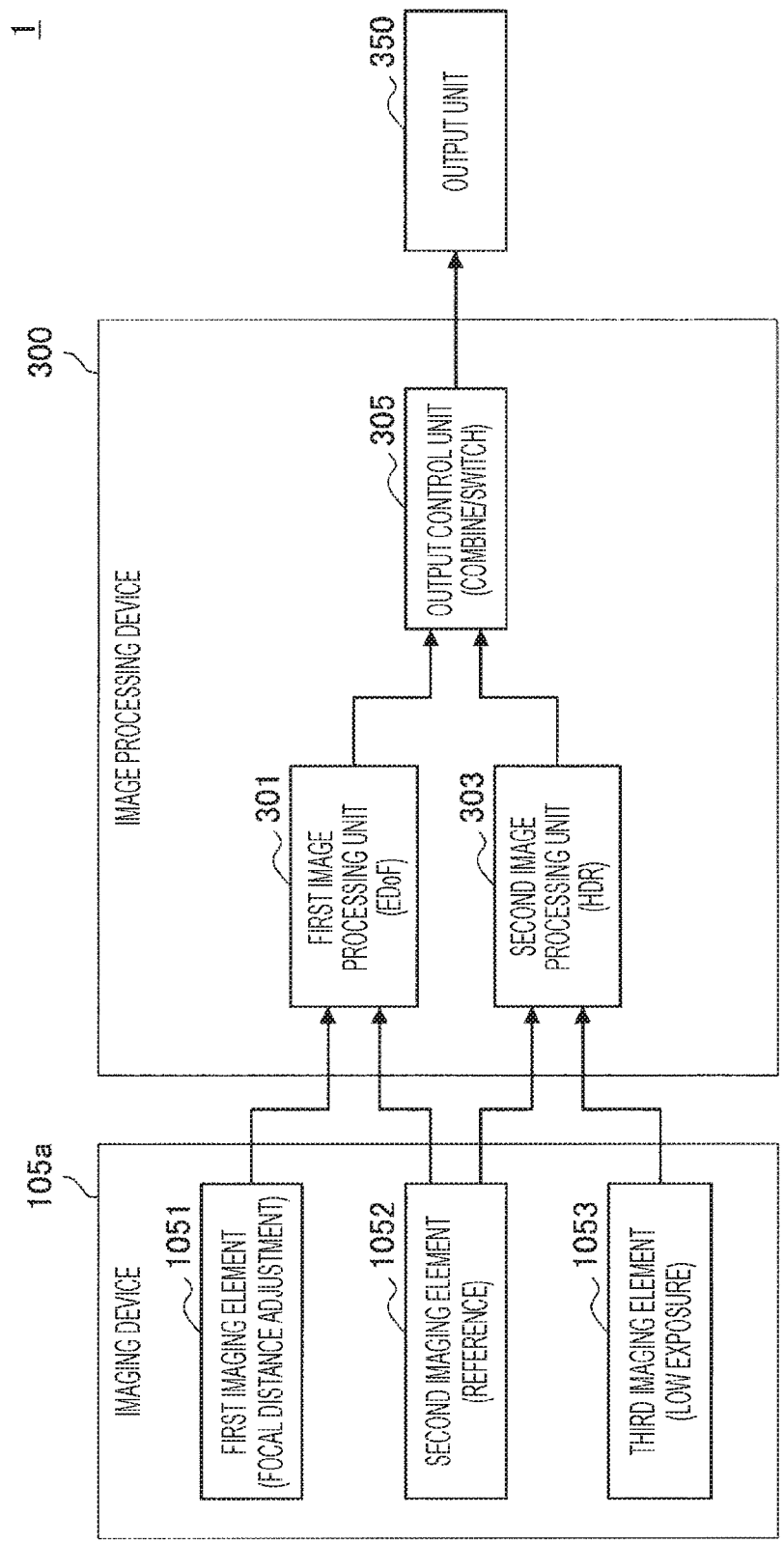
FIG. 5 is a block diagram illustrating an exemplary functional configuration of an imaging system of the embodiment.

Next, with reference to FIG. 5, an example of a schematic functional configuration of an imaging system according to the present embodiment will be described with a particular focus on a configuration of an image processing device that performs image processing on images captured by the imaging device 105a having been described with reference to FIG. 3. FIG. 5 is a block diagram illustrating an exemplary functional configuration of an imaging system according to the present embodiment.

As illustrated in FIG. 5, an imaging system 1 according to the present embodiment includes the imaging device 105a, an image processing device 300, and an output unit 350.

An imaging device 105a corresponds to the imaging device 105a having been described with reference to FIG. 3, and may correspond to, for example, the camera head 105 of the endoscope 101 in the endoscopic surgery system 100 illustrated in FIG. 1. As have been described with reference to FIG. 3, the imaging device 105a includes the first imaging element 1051 to the third imaging element 1053. Note that illustration of components other than the first imaging element 1051 to the third imaging element 1053 are omitted in FIG. 4 as the configuration of the imaging device 105a.

Moreover, in the example illustrated in FIG. 4, the first imaging element 1051 and the third imaging element 1053 are arranged using the second imaging element 1052 as a reference. Specifically, the first imaging element 1051 is arranged in such a manner that the distance from the branching optical system 211 (in other words, focal distance) illustrated in FIG. 3 is different from that of the second imaging element 1052. In addition, the imaging device 105a is configured in such a manner that the third imaging element 1053 captures an image having a lower exposure (that is, a darker image) than an image captured by the second imaging element 1052.

With such a configuration, each of the first imaging element 1051 to the third imaging element 1053 outputs a captured image to the image processing device 300. Note that in the following description images captured by the first imaging element 1051, the second imaging element 1052, and the third imaging element 1053 are also referred to as "a first image", "a second image", and "a third image", respectively.

The image processing device 300 generates an output image by performing various types of image processing on images captured by each of the first imaging element 1051 to the third imaging element 1053 of the imaging device 105a, and causes the output unit 350 to display the generated output image. The output unit 350 includes a so-called display or the like, and presents information to a user by displaying information to be presented such as an image as display information. Note that the image processing device 300 and the output unit 350 may correspond to, for example, the CCU 139 and the display device 141 in the endoscopic surgery system 100 illustrated in FIG. 1.

As a more specific example, the image processing device 300 includes a first image processing unit 301, a second image processing unit 303, and an output control unit 305 as illustrated in FIG. 4.

The first image processing unit 301 acquires a first image captured by the first imaging element 1051 and a second image captured by the second imaging element 1052. The first image processing unit 301 combines the first image and the second image by performing signal processing based on, for example, the EDoF technology on the acquired first image and second image to generate a composite image having a deeper depth of field than any of the first image and the second image (so-called EDoF image). Note that in the following description, a composite image generated by the first image processing unit 301 is also referred to as a "first composite image". The first image processing unit 301 outputs the generated first composite image to the output control unit 305.

The second image processing unit 303 acquires the second image captured by the second imaging element 1052 and a third image captured by the third imaging element 1053. The second image processing unit 303 combines the second image and the third image by performing signal processing based on, for example, the HDR technology on the acquired second image and third image to generate a composite image having a wider dynamic range than any of the second image and the third image (so-called HDR image). Note that in the following description, a composite image generated by the second image processing unit 303 is also referred to as a "second composite image". The second image processing unit 303 outputs the generated first composite image to the output control unit 305.

The output control unit 305 acquires the first composite image (EDoF image) based on the first image captured by the first imaging element 1051 and the second image captured by the second imaging element 1052 from the first image processing unit 301. The output control unit 305 further acquires the second composite image (HDR image) based on the second image captured by the second imaging element 1052 and the third image captured by the third imaging element 1053 from the second image processing unit 303. The output control unit 305 causes the output unit 350 to display an output image corresponding to at least one of the acquired first composite image or second composite image.

As one specific example, the output control unit 305 may generate a third composite image by combining the acquired first composite image and second composite image and cause the output unit 350 to display the generated third composite image. The third composite image generated in this manner has the characteristics of the first composite image (EDoF image) and the characteristics of the second composite image (HDR image). That is, such a configuration makes it possible to present the third composite image having a deeper depth of field and a wider dynamic range than any of the first to third images to a user via the output unit 350. Moreover, as another example, the output control unit 305 may cause the output unit 350 to display either the first composite image or the second composite image.

Furthermore, the output control unit 305 may selectively switch to one of two or more composite images, out of the first composite image to the third composite image described above, depending on a predetermined condition and cause the output unit 350 to display the selected composite image. As one specific example, the output control unit 305 may cause the output unit 350 to display one of the first composite image to the third composite image in accordance with an instruction from a user via a predetermined input unit (not illustrated). Furthermore, as still another example, the output control unit 305 may cause the output unit 350 to display one of the first composite image to the third composite image using a detection result of a predetermined event as a trigger.

In addition, the output control unit 305 may generate an output image in which two or more of the first composite image to the third composite images are presented, and cause the output unit 350 to display the generated output image. As one specific example, the output control unit 305 may generate an output image in which a part of the first composite image to the third composite image is presented as a partial image in a partial region of another composite image and cause the output unit 350 to display the output image.

Alternatively, in a case where a plurality of output units 350 is provided, the output control unit 305 may cause different output units 350 to separately display two or more composite images out of the first composite image to the third composite image.

Note that the above examples are merely illustrative, and a manner how to present (a) composite image(s) is not particularly limited as long as it is possible to present at least one of the first composite image to the third composite image to a user via the output unit 350.

The exemplary schematic functional configuration of the imaging system according to the present embodiment has been described with reference to FIG. 5 with a particular focus on the configuration of the image processing device that performs image processing on images captured by the imaging device 105a having been described with reference to FIG. 3.

3.3. Variations

Next, variations of the imaging device according to the present embodiment will be described.

First Variation: Example of Two-Plate Imaging Device

Figure 6:
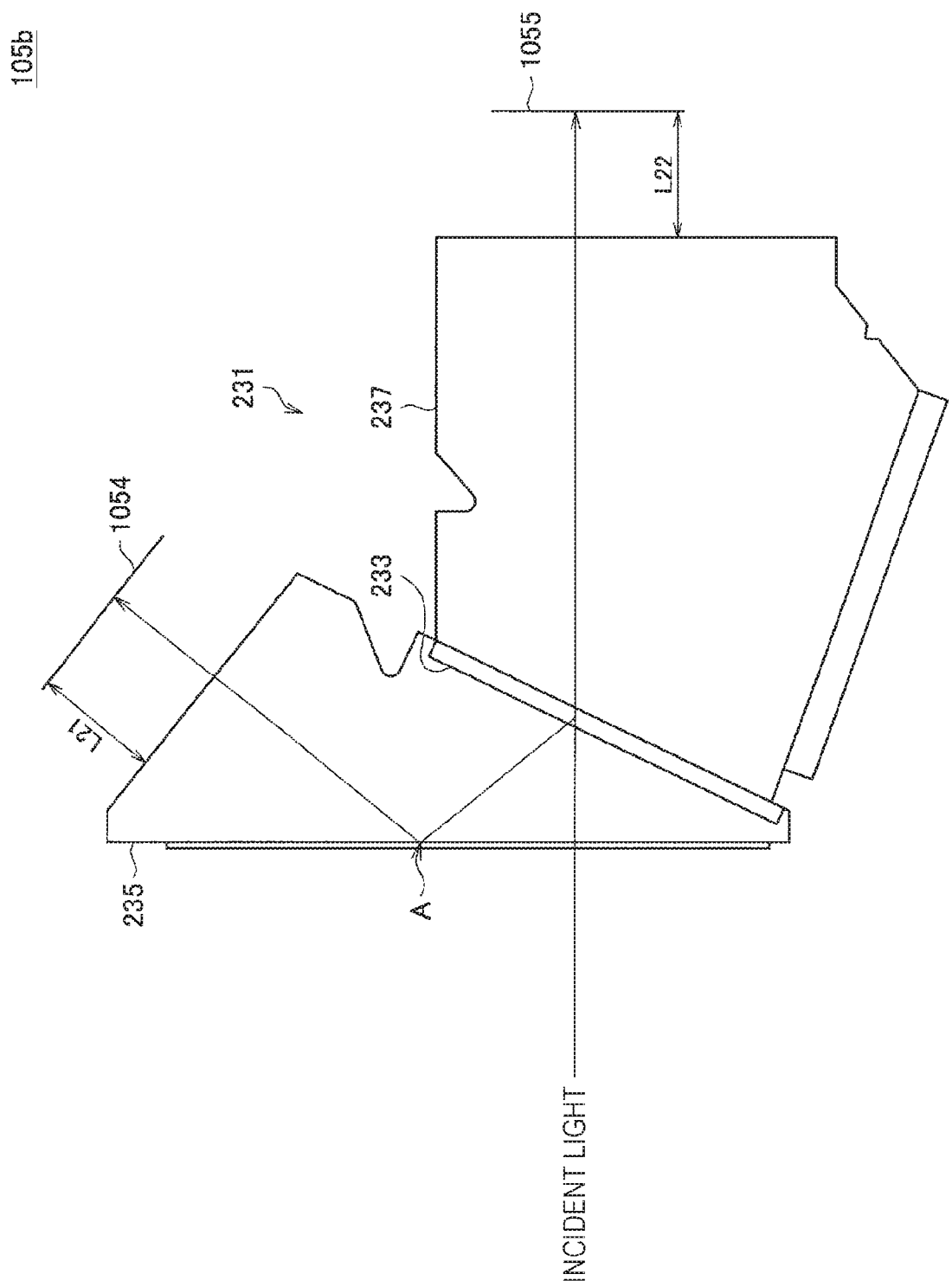
FIG. 6 is an explanatory diagram for explaining an exemplary configuration of an imaging device of a first variation.

First, as a first variation, an exemplary configuration of a two-plate imaging device will be described with reference to FIG. 6. FIG. 6 is an explanatory diagram for explaining an exemplary configuration of an imaging device of the first variation. Note that in the following description, an imaging device according to the present variation may be referred to as the "imaging device 105b" in order to distinguish from the imaging devices according to the embodiment described above and other variations.

As illustrated in FIG. 6, an imaging device 105b according to the first variation includes a branching optical system 231, a first imaging element 1054, and a second imaging element 1055.

The first imaging element 1054 and the second imaging element 1055 may have a structure similar to that of the first imaging element 1051 to the third imaging element 1053 in the imaging device 105a having been described above with reference to FIG. 3. That is, depending on the application of the imaging device 105b (for example, which of a color image and a black and white image is to be imaged), an imaging element having a Bayer array may be applied as the first imaging element 1054 and the second imaging element 1055, or an imaging element in which no color filter is provided may be applied. Incidentally, it is more preferable that the first imaging element 1054 and the second imaging element 1055 have a valid pixel number of a resolution higher than or equal to 4K.

The branching optical system 211 splits light incident on the imaging device 105a (that is, incident light) into a plurality of rays of light, and allows each of the split rays of light to form an image on each of the first imaging element 1054 and the second imaging element 1055.

Specifically, as illustrated in FIG. 6, the branching optical system 231 is a prism obtained by joining a first prism 235 and a second prism 237 via a beam splitter 233. That is, the beam splitter 233 is provided at the boundary between the first prism 235 and the second prism 237.

The beam splitter 233 splits the incident light into a plurality of rays of light by reflecting a part of the incident light. Note that the ratio between the light reflected by the beam splitter 233 and the light transmitted by the beam splitter 233 is determined depending on the reflectance (in other words, transmittance) of the beam splitter 233.

The first prism 235 is a prism which the incident light on the imaging device 105b enters, and functions as an optical path through which a part of the incident light reflected by the beam splitter 233 is guided. The second prism 237 functions as an optical path through which the light transmitted by the beam splitter 233 is guided.

The incident light incident on the first prism 235 travels straight through the first prism 235, and a part thereof is reflected by the beam splitter 233 provided obliquely on the optical axis, and the other part is transmitted by the beam splitter 233, thereby split into a plurality of rays of light.

The light reflected and split by the beam splitter 233 is guided in the first prism 235. Here, the light reflected and split is totally reflected only once at a position A illustrated in FIG. 5 and then is transmitted to the outside of the first prism 235. This allows the angle of the film-formed surface of the beam splitter 233 with respect to the optical axis to be closer to a right angle. Conversely, the installation angle of the beam splitter 233 according to the present variation on the optical axis is set in such a manner that the conditions for total reflection of visible light rays at the position A are satisfied. The light transmitted by the first prism 235 is guided to the first imaging element 1054. Note that another optical system may be interposed between the first prism 235 and the first imaging element 1054.

The light transmitted by the beam splitter 233 enters the second prism 237 and travels straight through the inside of the second prism 237. The end surface of the second prism 237 on the opposite side to the side where the beam splitter 233 is provided (in other words, the exit surface on the downstream side of the optical axis of the second prism 237) is perpendicular to the optical axis. Therefore, the light transmitted by the beam splitter 233 is transmitted to the outside of the second prism 237 while maintaining the state of being perpendicular to the exit surface of the second prism 237. The light transmitted by the second prism 237 is guided to the second imaging element 1055. Note that another optical system may be interposed between the second prism 237 and the second imaging element 1055.

Moreover, the imaging device 105b according to the present variation is configured in such a manner that the first imaging element 1054 and the second imaging element 1055 capture images having mutually different brightness. As one specific example, the imaging device 105b may be configured in such a manner that the first imaging element 1054 captures an image having a lower exposure (that is, a darker image) than an image captured by the second imaging element 1055. With such a configuration, for example by combining the images having mutually different brightness, captured by each of the second imaging element 1055 and the first imaging element 1054, it becomes possible to generate an image having a wider dynamic range than each of the images (for example, HDR image). Note that the configuration is not particularly limited as long as images having mutually different brightness are captured by the first imaging element 1054 and the second imaging element 1055.

Moreover, in the imaging device 105b according to the present variation, the first imaging element 1054 and the second imaging element 1055 are arranged in such a manner that the optical distances (in other words, focal distances) from the branching optical system 231 are different from each other. More specifically, the branching optical system 231 is telecentric on both sides, and the first imaging element 1054 and the second imaging element 1055 are arranged in such a manner that the optical distances from exit ends of the branching optical system 231 are different from each other. In other words, it can be said that the first imaging element 1054 and the second imaging element 1055 have mutually different focal distances using the branching optical system 231 as a reference.

For example, in FIG. 6, symbol L21 denotes an optical distance between an exit end of the branching optical system 231 (first prism 235) from which light that forms an image on the first imaging element 1054 exits and the first imaging element 1054. In addition, symbol L22 denotes an optical distance between an exit end of the branching optical system 231 (second prism 237) from which light that forms an image on the second imaging element 1055 exits and the second imaging element 1055. That is, in the example illustrated in FIG. 6, the first imaging element 1054 and the second imaging element 1055 are arranged in such a manner that the optical distance L21 and the optical distance L22 become different from each other.

With such a configuration, for example by combining images captured by each of the first imaging element 1054 and the second imaging element 1055 having different optical distances from the branching optical system 231 (that is, images of subjects having mutually different subject distances are formed thereon), it becomes possible to generate an image having a deeper depth of field (for example, EDoF image) than each of the above images.

With such a configuration, by combining images captured by each of the first imaging element 1054 and the second imaging element 1055, it becomes possible to acquire an image having a wider dynamic range and a deeper depth of field than each of the above images.

The exemplary configuration of the two-plate imaging device has been described above as the first variation with reference to FIG. 6.

Second Variation: Another Example of Three-Plate Imaging Device

Figure 7:
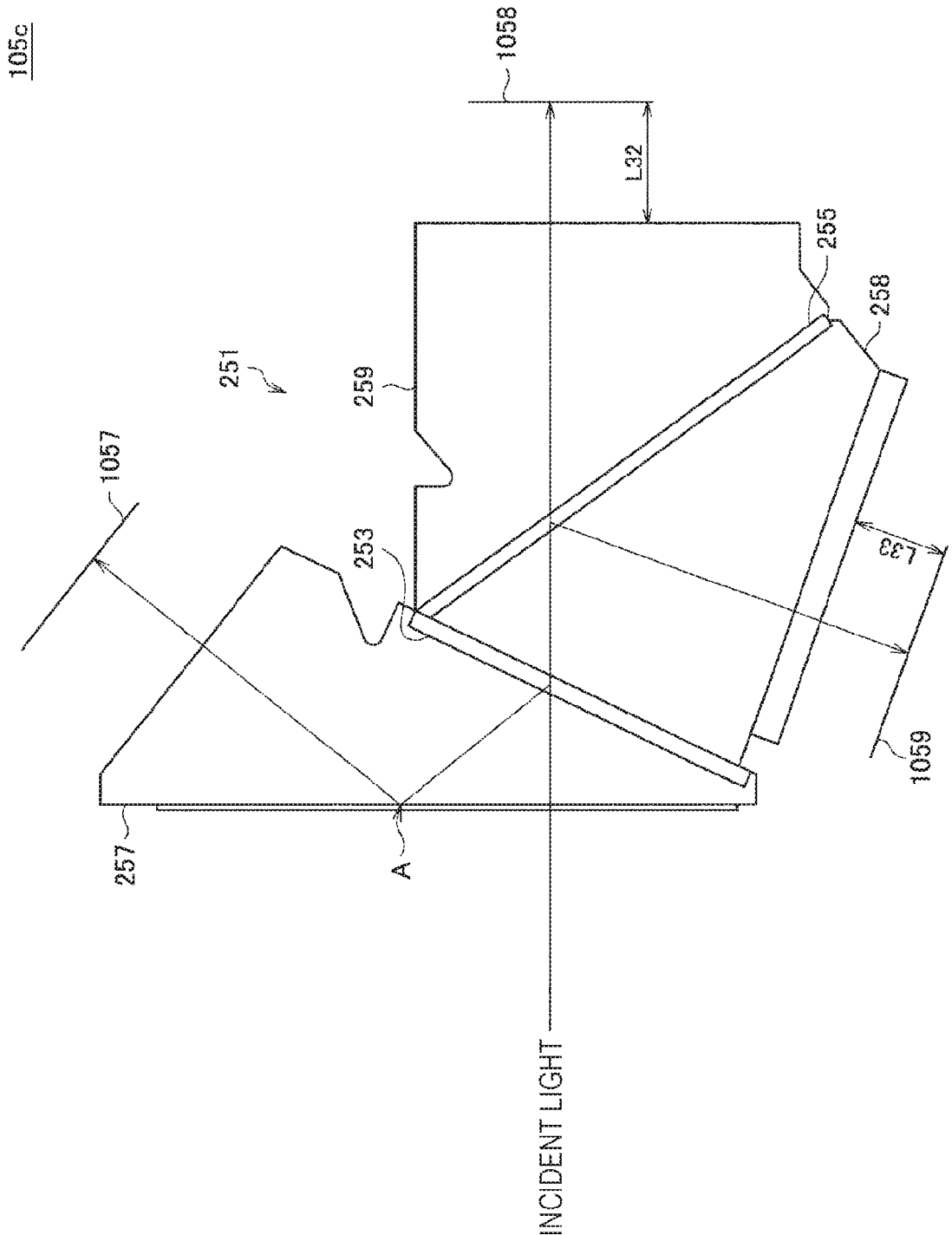
FIG. 7 is an explanatory diagram for explaining an exemplary configuration of an imaging device of a second variation.

Subsequently, as a second variation, another example of a three-plate imaging device will be described with reference to FIG. 7. FIG. 7 is an explanatory diagram for explaining an exemplary configuration of an imaging device of the second variation. Note that in the following description, an imaging device according to the present variation may be referred to as the "imaging device 105c" in order to distinguish from the imaging devices according to the embodiment described above and other variations.

As illustrated in FIG. 7, an imaging device 105c according to the second variation includes a branching optical system 251 and first to third imaging elements 1057 to 1059.

The branching optical system 251 splits light incident on the imaging device 105c (that is, incident light) into a plurality of rays of light, and allows each of the split rays of light to form an image on each of the first imaging element 1057 to the third imaging element 1059.

Specifically, as illustrated in FIG. 7, the branching optical system 251 is a prism obtained by joining a first prism 257 and a second prism 258 via a dichroic film 253 and joining the second prism 258 and a third prism 259 via a beam splitter 255. That is, the dichroic film 253 is provided at the boundary between the first prism 257 and the second prism 258. Likewise, the beam splitter 255 is provided at the boundary between the second prism 258 and the third prism 259.

The dichroic film 253 is an optical film for splitting light incident on the imaging device 105c (that is, incident light) into light belonging to a partial wavelength band among light belonging to visible light wavelength bands, and light belonging to other wavelength bands other than the partial wavelength band. As one specific example, the dichroic film 253 has a characteristic of reflecting, out of light belonging to visible light wavelength bands, light belonging to a wavelength bands including the R component (red component) and the B component (blue component) and transmitting light belonging to a wavelength band including the G component (green component).

Figure 8:
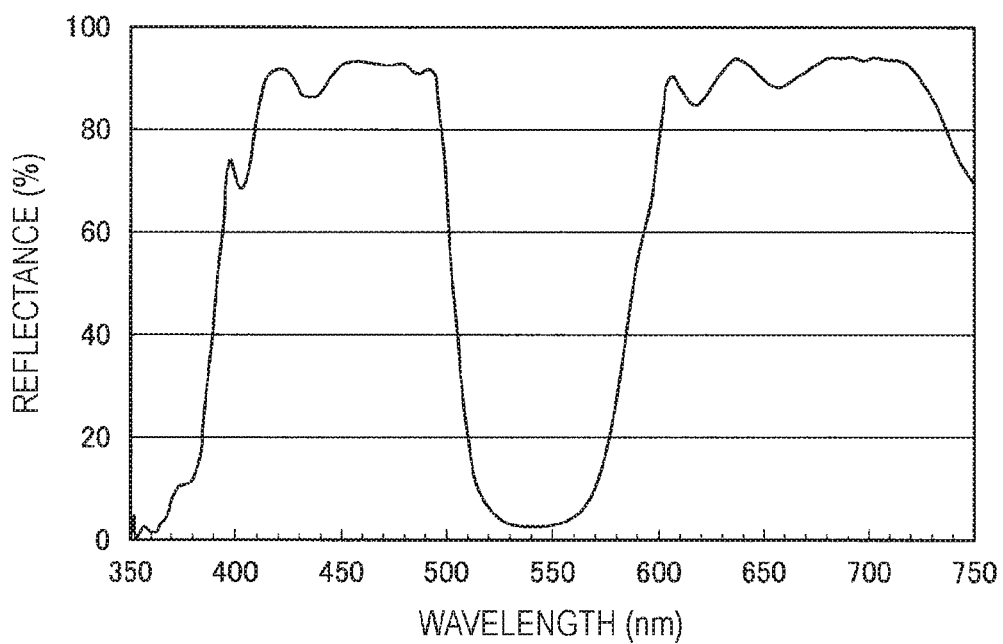
FIG. 8 is a graph illustrating an example of spectral characteristics of a dichroic film 253 applied to the imaging device of the second variation.
Figure 9:
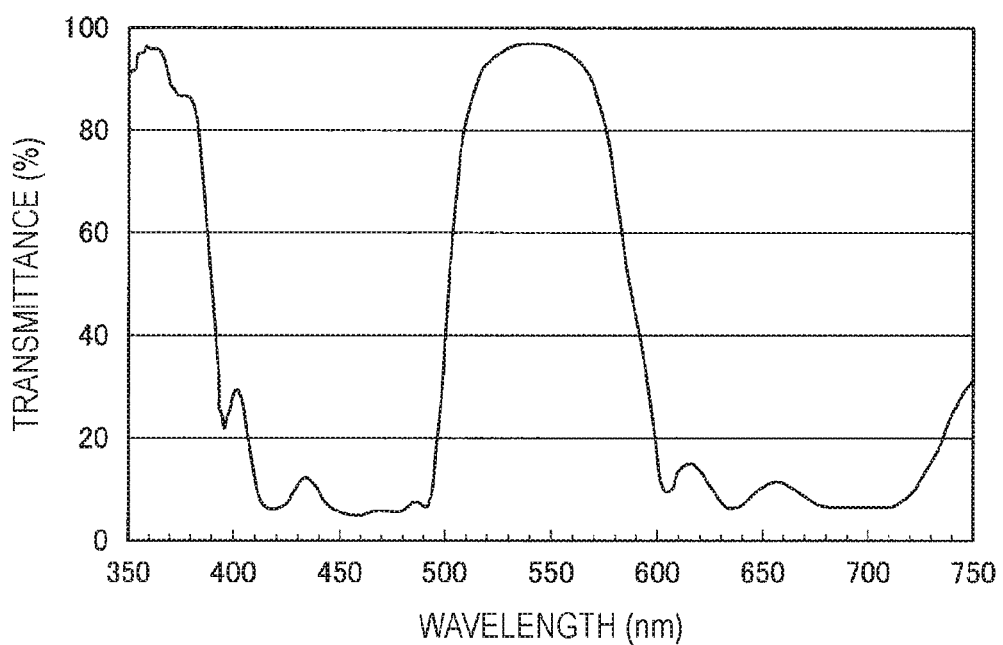
FIG. 9 is a diagram illustrating an example of spectral characteristics of the dichroic film 253 applied to the imaging device of the second variation.

For example, FIGS. 8 and 9 are graphs illustrating an example of spectral characteristics of the dichroic film 253 applied to the imaging device of the second variation. Specifically, FIG. 8 is a graph illustrating an example of characteristics of the spectral reflectance of the dichroic film 253. That is, in FIG. 8, the horizontal axis represents the wavelength (nm), and the vertical axis represents the spectral reflectance (%). Meanwhile, FIG. 9 is a graph illustrating an example of characteristics of the spectral transmittance of the dichroic film 253. That is, in FIG. 9, the horizontal axis represents the wavelength (nm), and the vertical axis represents the spectral transmittance (%). As illustrated in FIGS. 8 and 9, the dichroic film 253 has characteristics of reflecting most (e.g. more than or equal to 90%) of light in wavelength bands including the R component and the B component among the light of the three primary colors of the R component, the G component, and the G component, and transmitting most (e.g. more than or equal to 90%) of light in a wavelength band including the G component.

The first prism 257 is a prism which the incident light on the imaging device 105c enters and functions as an optical path through which the light belonging to the wavelength bands including the R component and the B component reflected by the dichroic film 253 is guided. The second prism 258 is a prism which the light belonging to the wavelength band including the G component transmitted by the dichroic film 253 enters and functions as an optical path through which a part of the light reflected by the beam splitter 255 is guided. The third prism 259 functions as an optical path through which the light transmitted by the beam splitter 255 (that is, another part of the light belonging to the wavelength band including the G component) is guided.

The incident light incident on the first prism 257 travels straight in the first prism 257 and then is split into the light belonging to the wavelength bands including the R component and the B component and the light belonging to the wavelength band including the G component by the dichroic film 253 provided obliquely on the optical axis. Note that in the following description, of the rays of light split from the incident light by the dichroic film 253, the light belonging to the wavelength bands including the R component and the B component is also referred to as "first light", and the light belonging to the wavelength band including the G component is also referred to as "second light" for the sake of convenience.

The first light is reflected by the dichroic film 253 and is guided in the first prism 257. Here, the first light reflected and split is totally reflected only once at a position A illustrated in FIG. 7 and then is transmitted to the outside of the first prism 257. This allows the angle of the film-formed surface of the dichroic film 253 with respect to the optical axis to be closer to a right angle. Conversely, the installation angle of the dichroic film 253 according to the present variation on the optical axis is set in such a manner that the conditions for total reflection of visible light rays at the position A are satisfied. The light transmitted by the first prism 257 is guided to the first imaging element 1057. Note that another optical system may be interposed between the first prism 257 and the first imaging element 1057.

The second light transmitted by the dichroic film 253 enters the second prism 258. The second light incident on the second prism 258 travels straight in the second prism 258, and a part thereof is reflected by the beam splitter 255 provided obliquely on the optical axis, and the other part is transmitted by the beam splitter 255, thereby split into a plurality of rays of light.

The light reflected and split by the beam splitter 255 (i.e. a part of the second light) is guided in the second prism 258. The end surface of the second prism 258 on the opposite side to the side where the beam splitter 255 is provided (in other words, the exit surface on the downstream side of the optical axis of the second prism 258) is perpendicular to the optical axis. Therefore, the light reflected and split by the beam splitter 255 is transmitted to the outside of the second prism 258 while maintaining the state of being perpendicular to the exit surface of the second prism 258. The light transmitted by the second prism 258 is guided to the third imaging element 1059. Note that another optical system may be interposed between the second prism 258 and the third imaging element 1059.

The light transmitted by the beam splitter 255 (i.e. the other part of the second light) enters the third prism 259 and travels straight inside the third prism 259. The end surface of the third prism 259 on the opposite side to the side where the beam splitter 255 is provided (in other words, the exit surface on the downstream side of the optical axis of the third prism 259) is perpendicular to the optical axis. Therefore, the light transmitted by the beam splitter 255 is transmitted to the outside of the third prism 259 while maintaining the state of being perpendicular to the exit surface of the third prism 259. The light transmitted by the third prism 259 is guided to the second imaging element 1058. Note that another optical system may be interposed between the third prism 259 and the second imaging element 1058.

As described above, of the rays of light obtained by splitting the incident light by the dichroic film 253, the first light reflected and split by the dichroic film 253 forms an image on the first imaging element 1057. Therefore, for example in a case where the dichroic film 253 reflects light belonging to the wavelength bands including the R component and the B component, the first imaging element 1057 includes at least R pixels and B pixels.

As a more specific example, only R pixels and B pixels may be arrayed in the first imaging element 1057. Furthermore, as another example, R pixels, B pixels, and G pixels may be arrayed in the first imaging element 1057. In this case, for example, an imaging element having a Bayer array may be applied as the first imaging element 1057. Incidentally, it is more preferable that the first imaging element 1057 has a valid pixel number of a resolution higher than or equal to 4K. Note that the first imaging element 1057 on which the first light forms an image corresponds to an example of a "sixth imaging element".

As described above, of the rays of light obtained by splitting the incident light by the dichroic film 253, the second light transmitted by the dichroic film 253 is split by the beam splitter 255 into two, each forming an image on the second imaging element 1058 and the third imaging element 1059. More specifically, partial light of the second light transmitted by the beam splitter 255 forms an image on the second imaging element 1058. Meanwhile, the other partial light of the second light reflected and split by the beam splitter 255 forms an image on the third imaging element 1059. Therefore, for example in a case where the dichroic film 253 reflects light belonging to the wavelength bands including the R component and the B component, the light belonging to the wavelength band including the G component forms an image on the second imaging element 1058 and the third imaging element 1059.

With such a configuration, it is preferable that, for example, imaging elements not including a color filter be applied as the second imaging element 1058 and the third imaging element 1059. In addition, as another example, an imaging element in which R pixels, B pixels, and G pixels are arrayed may be applied as at least one of the second imaging element 1058 or the third imaging element 1059. In this case, for example, an imaging element having a Bayer array may be applied as the above imaging element. Incidentally, it is more preferable that the second imaging element 1058 and the third imaging element 1059 have a valid pixel number of a resolution higher than or equal to 4K. Note that each of the rays of light split from the second light by the beam splitter 255 corresponds to an example of "third light" and "fourth light". In addition, the second imaging element 1058 and the third imaging element 1059 on which each of the rays of light split from the second light by the beam splitter 255 (that is, the third light and the fourth light) forms an image correspond to an example of a "fourth imaging element" and a "fifth imaging element".

Moreover, the imaging device 105c according to the present variation is configured in such a manner that the second imaging element 1058 and the third imaging element 1059 capture images having mutually different brightness. As one specific example, the imaging device 105c may be configured in such a manner that the third imaging element 1059 captures an image having a lower exposure (that is, a darker image) than an image captured by the second imaging element 1058. With such a configuration, for example by combining images captured by each of the first imaging element 1057, the second imaging element 1058, and the third imaging element 1059, it becomes possible to generate an image having a wider dynamic range than each of the above images (for example, HDR image). Note that the configuration is not particularly limited as long as images having mutually different brightness are captured by the second imaging element 1058 and the third imaging element 1059.

Moreover, in the imaging device 105c according to the present variation, the second imaging element 1058 and the third imaging element 1059 are arranged in such a manner that the optical distances (in other words, focal distances) from the branching optical system 251 are different from each other. More specifically, the branching optical system 251 is telecentric on both sides, and the second imaging element 1058 and the third imaging element 1059 are arranged in such a manner that the optical distances from exit ends of the branching optical system 251 are different from each other. In other words, it can be said that the second imaging element 1058 and the third imaging element 1059 have different focal distances using the branching optical system 251 as a reference.

For example, in FIG. 6, symbol L32 denotes an optical distance between an exit end of the branching optical system 251 (third prism 259) from which light that forms an image on the second imaging element 1058 exits and the second imaging element 1058. In addition, symbol L33 denotes an optical distance between an exit end of the branching optical system 251 (second prism 258) from which light that forms an image on the third imaging element 1059 exits and the third imaging element 1059. That is, in the example illustrated in FIG. 7, the second imaging element 1058 and the third imaging element 1059 are arranged in such a manner that the optical distance L32 and the optical distance L33 become different from each other. Note that the optical distance between the branching optical system 251 and the first imaging element is not particularly limited. As one specific example, the first imaging element may be arranged in such a manner that the optical distance between the branching optical system 251 and the first imaging element becomes substantially equal to the optical distance L32.

With such a configuration, for example by combining images captured by each of the first imaging element 1057, the second imaging element 1058, and the third imaging element 1059, it becomes possible to generate an image having a deeper depth of field than each of the above images (for example, EDoF image).

The other example of the three-plate imaging device has been described as the second variation with reference to FIGS. 7 to 9.

4. Exemplary Hardware Configuration

Figure 10:
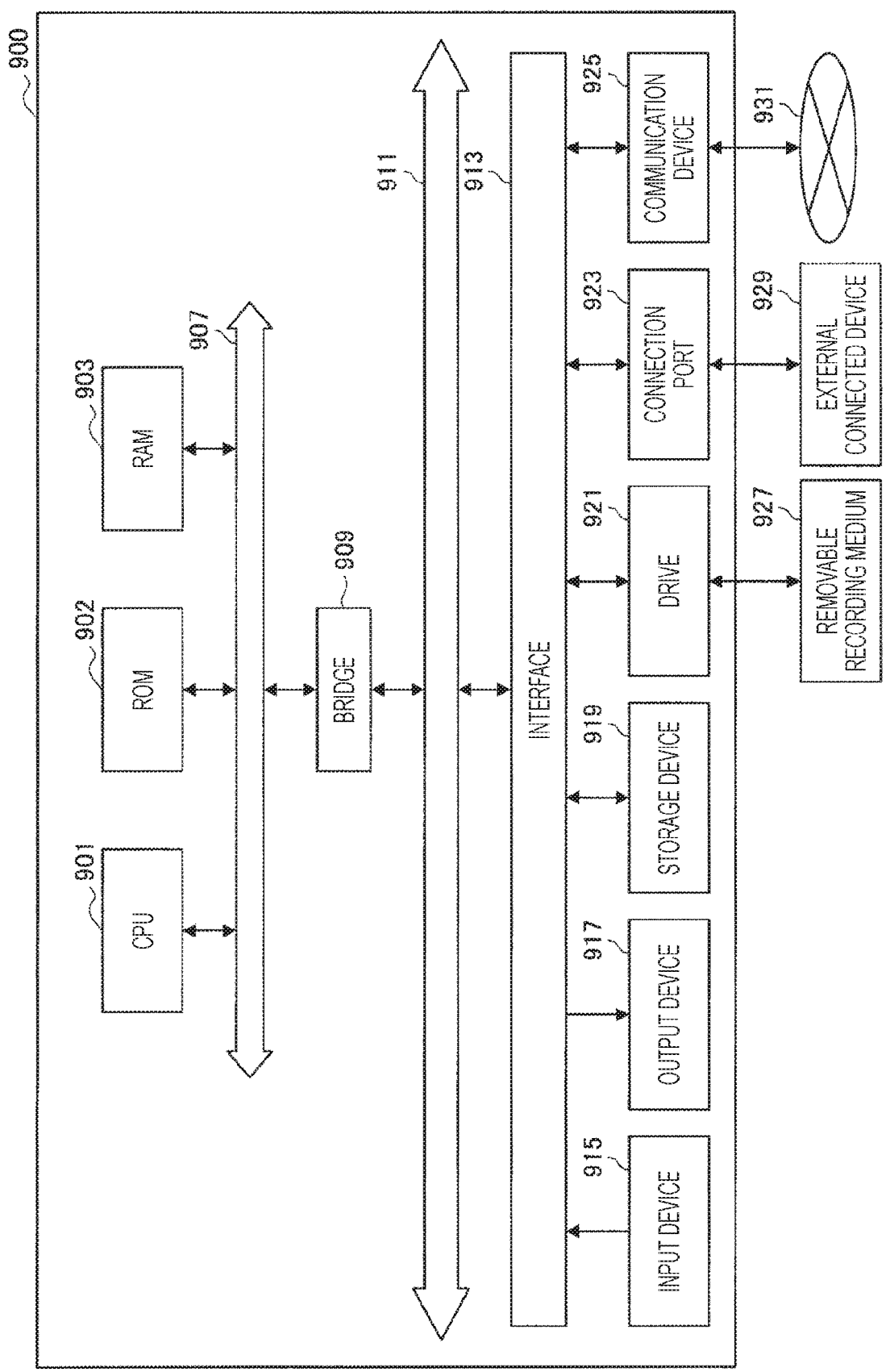
FIG. 10 is a functional block diagram illustrating an example of a hardware configuration of an information processing device included in an endoscope imaging system according to an embodiment of the present disclosure.

Subsequently, detailed description will be given with reference to FIG. 10 regarding an exemplary hardware configuration of an information processing device (for example, the image processing device) that executes various types of processing like the CCU in the endoscope imaging system (that is, endoscopic surgery system) described above. FIG. 10 is a functional block diagram illustrating an example of a hardware configuration of an information processing device included in the endoscope imaging system according to the embodiment of the present disclosure.

An information processing device 900 included in the endoscope imaging system according to the present embodiment mainly includes a CPU 901, a ROM 903, and a RAM 905. The information processing device 900 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls the entire operation of the information processing device 900 or a part thereof in accordance with various programs stored in the ROM 903, the RAM 905, a storage device 919, or a removable recording medium 927. The ROM 903 stores programs, arithmetic operation parameters, and the like to be used by the CPU 901. The RAM 905 primarily stores programs used by the CPU 901, parameters that change as appropriate upon execution of a program, and other data. These components are mutually coupled by a host bus 907 included in an internal bus such as a CPU bus.

The host bus 907 is coupled to an external bus 911 such as a peripheral component interconnect/interface (PCI) bus via a bridge 909. The external bus 911 is further coupled to the input device 915, the output device 917, the storage device 919, the drive 921, the connection port 923, and the communication device 925 via the interface 913.

The input device 915 is a means for operation that a user operates such as a mouse, a keyboard, a touch panel, a button, a switch, a lever, and a pedal. Also, the input device 915 may be, for example, a remote control means (a so-called remote controller) using infrared rays or other radio waves, or may be an external connected device 929 such as a mobile phone or a PDA supporting to the operation of the information processing device 900. The input device 915 further includes, for example, an input control circuit, or the like that generates an input signal on the basis of information having been input by the user using the above-described operation means, and outputs the input signal to the CPU 901. A user of the information processing device 900 can input various types of data or instruct processing operation to the information processing device 900 by operating the input device 915.

The output device 917 includes a device capable of visually or aurally notifying the user of the acquired information. Such devices include display devices such as CRT display devices, liquid crystal display devices, plasma display devices, EL display devices, and lamps, audio output devices such as speakers and headphones, printer devices, and the like. The output device 917 outputs, for example, a result obtained by various types of processing performed by the information processing device 900. Specifically, a display device displays a result obtained by various types of processing performed by the information processing device 900 as text or an image. Meanwhile, an audio output device outputs an analog signal by converting an audio signal including reproduced audio data, acoustic data or the like into the analog signal.

The storage device 919 is a device for storing data configured as an exemplary storage unit of the information processing device 900. The storage device 919 may include, for example, a magnetic storage device such as a hard disk drive (HDD), a semiconductor storage device, an optical storage device, a magneto-optical storage device, or the like. The storage device 919 stores programs to be executed by the CPU 901, various types of data, etc.

The drive 921 is a reader/writer for a recording medium, and is built in or externally attached to the information processing device 900. The drive 921 reads out information recorded in the removable recording medium 927 mounted thereto such as a magnetic disk, an optical disk, a magneto-optical disk, or a semiconductor memory, and outputs the information to the RAM 905. The drive 921 is also capable of writing a record in the removable recording medium 927 mounted thereto such as a magnetic disk, an optical disk, a magneto-optical disk, or a semiconductor memory. The removable recording medium 927 is, for example, a DVD medium, an HD-DVD medium, a Blu-ray (registered trademark) medium, or the like. In addition, the removable recording medium 927 may be a CompactFlash (CF) (registered trademark) card, a flash memory, a secure digital (SD) memory card, or the like. Furthermore, the removable recording medium 927 may be, for example, an integrated circuit (IC) card mounted with a non-contact type IC chip, an electronic device, or the like.

The connection port 923 is for direct connection to the information processing device 900. Examples of the connection port 923 include a universal serial bus (USB) port, an IEEE 1394 port, a small computer system interface (SCSI) port, and the like. Other examples of the connection port 923 include an RS-232C port, an optical audio terminal, a high-definition multimedia interface (HDMI) (registered trademark) port, and the like. Coupling the external connected device 929 to the connection port 923 allows the information processing device 900 to acquire various types of data directly from the external connected device 929 or to provide various types of data to the external connected device 929.

The communication device 925 is, for example, a communication interface including a communication device or the like for coupling to a communication network (network) 931. The communication device 925 is, for example, a communication card or the like for a wired or wireless local area network (LAN), Bluetooth (registered trademark), or wireless USB (WUSB). In addition, the communication device 925 may be a router for optical communication, a router for asymmetric digital subscriber line (ADSL), a modem for various types of communication, or the like. The communication device 925 is capable of transmitting and receiving signals or the like in accordance with a predetermined protocol such as the TCP/IP to and from the Internet or another communication device. In addition, the communication network 931 coupled to the communication device 925 includes networks or the like coupled in a wired or wireless manner, and may be, for example, the Internet, a home LAN, infrared communication, radio wave communication, satellite communication, etc.

The example of the hardware configuration which can implement the function of the information processing device 900 included in the endoscope imaging system according to the embodiment of the present disclosure has been illustrated. Each of the components described above may be a generic member, or may be hardware specialized for the function of each of the components. Therefore, it is possible to modify the hardware configuration to be used as appropriate depending on the technical level of the time of carrying out the present embodiment. Note that, although not illustrated in FIG. 10, naturally, various components corresponding to the information processing device 900 included in the endoscope imaging system are included.

Note that it is possible to create a computer program for implementing each function of the information processing device 900 included in the endoscope imaging system according to the present embodiment as described above and to implement the computer program in a personal computer or the like. Alternatively, it is also possible to provide a computer readable recording medium in which such a computer program is stored. The recording medium is, for example, a magnetic disk, an optical disk, a magneto-optical disk, a flash memory, or the like. Further alternatively, the above computer program may be distributed via, for example, a network without using a recording medium. Incidentally, the number of computers that execute the computer program is not particularly limited. For example, a plurality of computers (for example, a plurality of servers, or the like) may execute the computer program in cooperation with each other.

5. Application Examples

Subsequently, as an application example of the imaging system according to the embodiment of the present disclosure, an exemplary case where the imaging system is configured as a microscope imaging system including a microscope unit will be described with reference to FIG. 11.

Figure 11:
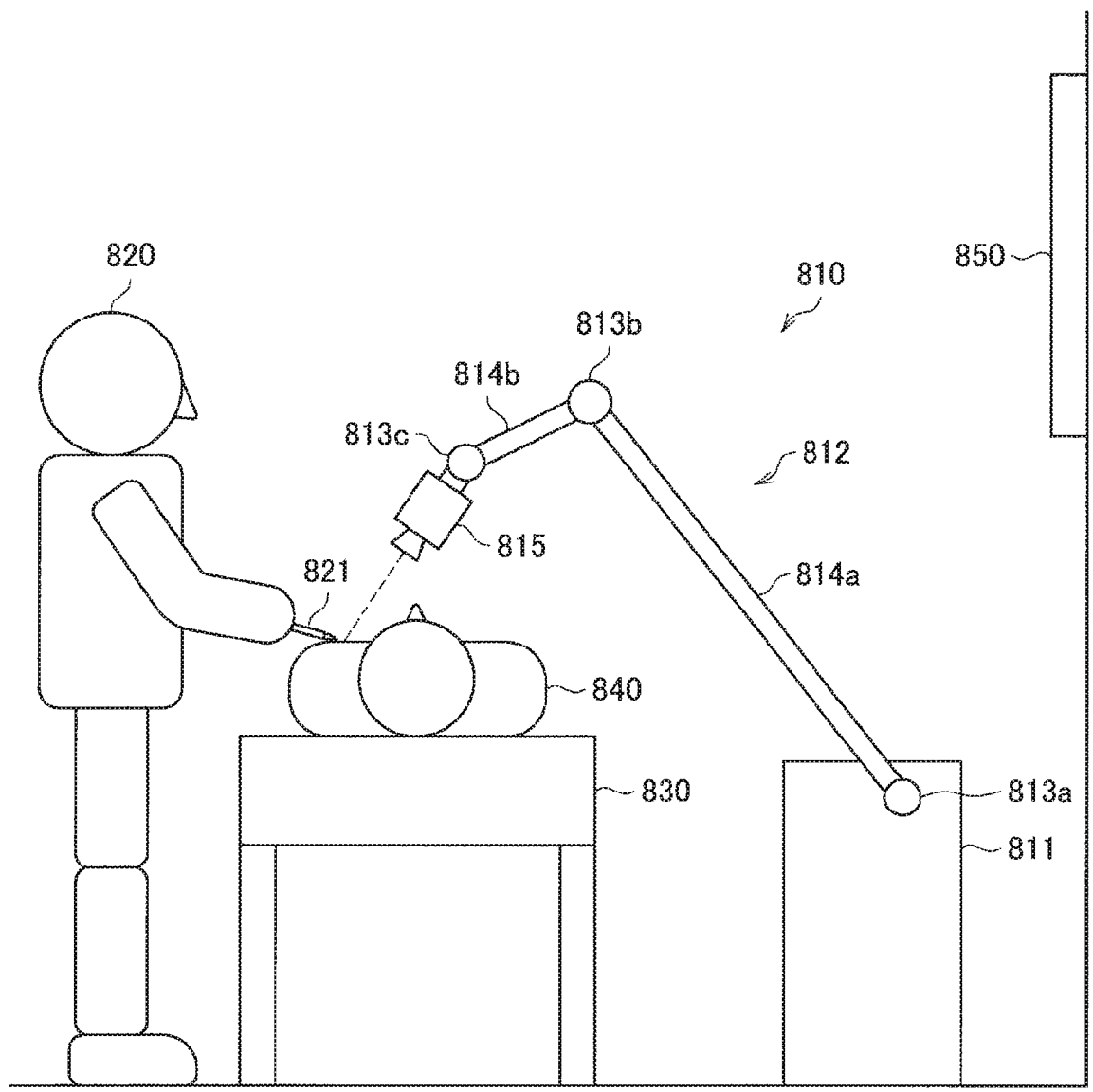
FIG. 11 is an explanatory diagram for explaining an application example of an imaging system according to an embodiment of the present disclosure.

FIG. 11 is an explanatory diagram for explaining an application example of the imaging system according to the embodiment of the present disclosure and illustrating an exemplary schematic configuration of a microscope imaging system. Specifically, an exemplary case is illustrated in FIG. 11 in which a surgical video microscope device including an arm is used as an application example in which a microscope imaging system according to an embodiment of the present disclosure is used.

For example, FIG. 11 is a diagram schematically illustrating the situation of treatment using a surgical video microscope device. Specifically, referring to FIG. 11, a situation is illustrated in which a surgeon as an operator (user) 820 is conducting an operation on an treatment subject (patient) 840 on an operating table 830 using a surgical instrument 821 such as a scalpel, a surgical tweezer, or forceps. Note that in the following description, the term "treatment" is a general term for various types of medical treatment which a surgeon, as the user 820, performs on a patient, as the treatment subject 840, such as surgery and examination. Furthermore, although the example illustrated in FIG. 11 illustrates the state of surgery is illustrated as an example of treatment, the treatment using the surgical video microscope device 810 is not limited to surgery, and may be other various types of treatment.

The surgical video microscope device 810 is installed beside the operating table 830. The surgical video microscope device 810 includes a base 811 which is a base, an arm 812 extending from the base 811, and an imaging unit 815 coupled to the tip of the arm 812 as a tip unit. The arm 812 includes a plurality of joints 813*a*, 813*b*, and 813*c*, a plurality of links 814*a* and 814*b* coupled by the joints 813*a* and 813*b*, and the imaging unit 815 provided at the tip of the arm 812. In the example illustrated in FIG. 11, the arm 812 has three joints 813*a* to 813*c* and two links 814*a* and 814*b* for the sake of simplicity; however, in practice the number and the shape of the joints 813*a* to 813*c* and the links 814*a* and 814*b*, directions of driving shafts of the joints 813*a* to 813*c*, etc. may be set as appropriate so as to implement a desired degree of freedom in consideration of the degree of freedom of the position and the attitude of the arm 812 and the imaging unit 815.

The joints 813*a* to 813*c* have a function of rotatably coupling the links 814*a* and 814*b* to each other, and the driving of the arm 812 is controlled by driving the rotation of the joints 813*a* to 813*c*. Here, in the following description, the position of each component of the surgical video microscope device 810 means the position (coordinates) in a space defined for drive control, and the attitude of each component means the direction (angle) with respect to any axis in the space defined for drive control. Moreover, in the following description, driving (or drive control) of the arm 812 means driving (or drive control) of the joints 813*a* to 813*c* and that the position and the attitude of each component of the arm 812 are changed (controlled to change) by driving (or drive control) of the joints 813*a* to 813*c*.

The imaging unit 815 is coupled to the tip of the arm 812 as a tip unit. The imaging unit 815 acquires an image of an imaging object, and is, for example, a camera, or the like capable of capturing a moving image or a still image. As illustrated in FIG. 11, the surgical video microscope device 810 controls the attitude or the position of the arm 812 and the imaging unit 815 so that the imaging unit 815 provided at the tip of the arm 812 captures an image of a treatment site of the treatment subject 840. Note that the configuration of the imaging unit 815 coupled to the tip of the arm 812 as a tip unit is not particularly limited. The imaging unit 815 is configured as, for example, a microscope that acquires an magnified image of an imaging object. Moreover, the imaging unit 815 may be attachable to and detachable from the arm 812. With such a configuration, for example, an imaging unit 815 corresponding to a usage application may be coupled to the tip of the arm 812 as a tip unit as appropriate. Note that, for example, an imaging device applied with the branching optical system according to the embodiment described above can be applied as the imaging unit 815. That is, in the present application example, the imaging unit 815 or the surgical video microscope device 810 including the imaging unit 815 may correspond to an example of the "medical observation device". Incidentally, the case in which the imaging unit 815 is applied as the tip unit has been focused and described in the present description; however, a tip unit coupled to the tip of the arm 812 is not necessarily limited to the imaging unit 815.

In addition, a display device 850 such as a monitor or a display is installed at a position facing the user 820. An image of the treatment site captured by the imaging unit 815 is displayed as an electronic image on a display screen of the display device 850. The user 820 performs various types of treatment while viewing the electronic image of the treatment site displayed on the display screen of the display device 850.

The configuration as described above allows an operation to be conducted while a treatment site is being captured by the surgical video microscope device 810.

6. Conclusion

As described above, the imaging system according to the present embodiment includes the imaging system (for example, the camera head 105 illustrated in FIGS. 1 and 2) and the image processing device (for example, the CCU 139 illustrated in FIGS. 1 and 2) for performing image processing on images captured by the imaging device. The imaging device includes a plurality of imaging elements and a branching optical system that splits incident light into a plurality of rays of light. Moreover, each of the multiple rays of light split by the branching optical system is guided (or forms an image) to at least one of the multiple imaging elements. On the basis of such a configuration, two or more imaging elements out of the plurality of imaging elements each capture images having mutually different brightness, and two or more imaging elements are arranged so as to have mutually different optical distances from the branching optical system. The image processing device may generate, for example on the basis of the multiple images having mutually different brightness, a first composite image having a wider dynamic range than each of the multiple images. Furthermore, as another example, the image processing device may generate a second composite image having a deeper depth of field than each of multiple images on the basis of the multiple images captured by each of the two or more imaging elements having mutually different optical distances from the branching optical system. Note that the image processing device may selectively generate one or both of the first composite image and the second composite image. Alternatively, the image processing device may also generate a third composite image by combining the first composite image and the second composite image.

With such a configuration, according to the imaging system of the present embodiment, for example, it is also possible to selectively acquire at least one of an image having a wider dynamic range or an image having a deeper depth of field depending on the situation. Furthermore, according to the imaging system according to the present embodiment, it is also possible to acquire an image having a wider dynamic range and a deeper depth of field. That is, the imaging system of the present embodiment enables acquisition of a high quality image in a more preferable manner even under a situation where a higher resolution image is captured using high definition imaging elements.

In addition, as described above, incident light is split by the branching optical system, and each rays of light split from the incident light forms an image on each of the multiple imaging elements in the imaging system according to the present embodiment. Due to such a configuration, according to the imaging system, it becomes possible to suppress a parallax generated between multiple images (ideally, no parallax generated) as compared with a system obtained by combining a plurality of functions. With such a configuration, the imaging system also allows spatial resolution and temporal resolution to be further improved as compared to a case where HDR or other technology is implemented using one imaging element. In addition, the imaging system can implement a plurality of functions by itself, thereby enabling further miniaturization as compared with a system obtained by combining a plurality of functions.

The preferred embodiments of the present disclosure have been described in detail with reference to the accompanying drawings; however, the technical scope of the present disclosure is not limited to such examples. It is clear that a person having ordinary knowledge in the technical field of the present disclosure can conceive various variations or modifications within the scope of the technical idea described in the claims, and it is understood that these variations or modifications also naturally belong to the technical scope of the present disclosure.

For example, in the above embodiment, exemplary configurations for generating a higher quality image by focusing on EDoF and HDR have been described. Meanwhile, as long as it is possible to generate a higher quality image by combining a plurality of images, a method therefor is not necessarily limited to EDoF or HDR. That is, a configuration of an imaging device or the content of processing related to image composition is not limited as long as it is possible to generate an image, having a higher quality than images captured by each of the multiple imaging elements included in the imaging device according to the present embodiment, on the basis of the above images.

In addition, the effects described herein are merely illustrative or exemplary, and not limiting. That is, the technology according to the present disclosure may exert other effects apparent to those skilled in the art from the description of the present specification, together with or in place of the above effects.

Note that the following configurations are also within the technical scope of the present disclosure.

(1)

A medical observation system including:

a medical observation device; and an image processing device configured to perform image processing on an image captured by the medical observation device, in which the medical observation device includes a plurality of imaging elements and a branching optical system configured to split incident light into a plurality of rays of light, each of the plurality of rays of light split by the branching optical system is guided to at least one of the plurality of imaging elements, of the plurality of imaging elements, two or more imaging elements each capture images having mutually different brightness, and two or more imaging elements are arranged so as to have mutually different optical distances from the branching optical system, and the image processing device generates at least one of a first composite image based on a plurality of images having mutually different brightness, the first composite image having a wider dynamic range than each of the plurality of images, or a second composite image based on a plurality of images captured by each of the two or more imaging elements having different optical distances from the branching optical system, the second composite image having a deeper depth of field than each of the plurality of images.

(2)

The medical observation system according to the item (1), in which, of the plurality of imaging elements, a first imaging element and a second imaging element capture the images having mutually different brightness, and the first imaging element and the second imaging element are arranged so as to have mutually different optical distances from the branching optical system.

(3)

The medical observation system according to the item (1), in which, of the plurality of imaging elements, a first imaging element and a second imaging element capture the images having mutually different brightness, and of the plurality of imaging elements, the first imaging element and a third imaging element different from the second imaging element are arranged so as to have mutually different optical distances from the branching optical system.

(4)

The medical observation system according to the item (1), in which the branching optical system includes:

a dichroic film that splits first light belonging to a predetermined wavelength band from the incident light; and a beam splitter that splits second light, obtained by splitting the first light from the incident light, into third light and fourth light, of the plurality of imaging elements, a fourth imaging element through which the third light is guided and a fifth imaging element through which the fourth light is guided capture the images having mutually different brightness, and the fourth imaging element and the fifth imaging element are arranged so as to have mutually different optical distances from the branching optical system.

(5)

The medical observation system according to the item (4), in which the fourth imaging element and the fifth imaging element are not provided with a color filter.

(6)

The medical observation system according to the item (4) or (5), in which the second light belongs to a partial wavelength band among visible light wavelength bands.

(7)

The medical observation system according to the item (6), in which the second light includes light belonging to a wavelength band of a G component, and the first light includes light belonging to wavelength bands of each of an R component and a B component.

(8)

The medical observation system according to any one of the items (4) to (7) in which, of the plurality of imaging elements, a sixth imaging element through which the first light is guided has a Bayer array.

(9)

The medical observation system according to any one of the items (1) to (8), in which an image captured by at least one of the plurality of imaging elements has a resolution higher than or equal to 4K.

(10)

The medical observation system according to any one of the items (1) to (9), in which acquisition conditions of the plurality of images, from which the first composite image is generated, are different in at least one of an amount of light guided to the corresponding imaging elements or sensitivity or a shutter speed of the imaging elements.

(11)

The medical observation system according to the item (10), in which the incident light is split in such a manner that rays of light of different amounts are guided to two or more imaging elements that capture the images from which the first composite image is generated.

(12)

The medical observation system according to the item (10), in which rays of light of different amounts are guided to each of two or more imaging elements that capture the images, from which the first composite image is generated, through control of a diaphragm provided as a preceding stage of each of the two or more imaging elements.

(13)

The medical observation system according to any one of the items (1) to (12), in which, of the plurality of imaging elements, two or more imaging elements that capture the images, from which the second composite image is generated, are arranged so as to have mutually different optical distances from exit ends of the branching optical system.

(14)

The medical observation system according to any one of the items (1) to (13), in which the image processing device generates a third composite image on the basis of the first composite image and the second composite image.

(15)

The medical observation system according to any one of the items (1) to (14), in which the medical observation device includes an endoscope unit including a lens barrel to be inserted into a body cavity of a subject, and captures an image of the subject acquired by the endoscope unit.

(16)

The medical observation system according to any one of the items (1) to (14), in which the medical observation device further includes a microscope unit configured to acquire a magnified image of an imaging object, and captures an image of the imaging object acquired by the microscope unit.

(17)

A medical observation device including:

a plurality of imaging elements; and a branching optical system configured to split incident light into a plurality of rays of light, in which each of the plurality of rays of light split by the branching optical system is guided to at least one of the plurality of imaging elements, and of the plurality of imaging elements, two or more imaging elements capture images having mutually different brightness, and two or more imaging elements have different optical distances from the branching optical system.

REFERENCE SIGNS LIST

1 Imaging system
105a Imaging device
211 Branching optical system
213 Beam splitter
215 Beam splitter
217 First prism
218 Second prism
219 Third prism
1051 First imaging element
1052 Second imaging element
1053 Third imaging element
105b Imaging device
231 Branching optical system
233 Beam splitter 235 First prism
237 Second prism
1054 First imaging element
1055 Second imaging element
105c Imaging device
251 Branching optical system
253 Dichroic film
255 Beam splitter
257 First prism
258 Second prism
259 Third prism
1057 First imaging element
1058 Second imaging element
1059 Third imaging element
300 Image processing device
301 First image processing unit
303 First image processing unit
303 Second image processing unit
305 Output control unit
350 Output unit

The invention claimed is:

1. A medical observation system, comprising:
a medical observation device configured to capture an image; and
an image processing device configured to perform image processing on the image captured by the medical observation device, wherein
the medical observation device includes a plurality of imaging elements and a branching optical system configured to split incident light into a plurality of rays of light,
each of the plurality of rays of light split by the branching optical system is guided to at least one of the plurality of imaging elements,
two or more imaging elements of the plurality of imaging elements capture images having mutually different brightness, and two or more imaging elements have mutually different optical distances from the branching optical system,
the image processing device is further configured to generate at least one of a first composite image based on a plurality of images having mutually different brightness or a second composite image based on a plurality of images captured by each of the two or more imaging elements having different optical distances from the branching optical system,
the first composite image has a wider dynamic range than each of the plurality of images, and
the second composite image has a deeper depth of field than each of the plurality of images,
the branching optical system includes a beam splitter configured to split second light into third light and fourth light,
the second light is obtained based on split of first light associated with a specific wavelength band from the incident light, and
of the plurality of imaging elements, a fourth imaging element through which the third light is guided and a fifth imaging element through which the fourth light is guided capture the images having mutually different brightness.

2. The medical observation system according to claim 1, wherein
a first imaging element and a second imaging element of the plurality of imaging elements capture the images having mutually different brightness, and
the first imaging element and the second imaging element have mutually different optical distances from the branching optical system.

3. The medical observation system according to claim 1, wherein
a first imaging element and a second imaging element of the plurality of imaging elements capture the images having mutually different brightness, and
of the plurality of imaging elements, the first imaging element and a third imaging element different from the second imaging element have mutually different optical distances from the branching optical system.

4. The medical observation system according to claim 1, wherein the branching optical system further includes:
a dichroic film configured to split the first light belonging to the specific wavelength band from the incident light, wherein
the fourth imaging element and the fifth imaging element have mutually different optical distances from the branching optical system.

5. The medical observation system according to claim 4, wherein the fourth imaging element and the fifth imaging element are not provided with a color filter.

6. The medical observation system according to claim 4, wherein the second light belongs to a partial wavelength band among visible light wavelength bands.

7. The medical observation system according to claim 6, wherein
the second light includes light belonging to a wavelength band of a G component, and
the first light includes light belonging to wavelength bands of each of an R component and a B component.

8. The medical observation system according to claim 4, wherein of the plurality of imaging elements, a sixth imaging element through which the first light is guided has a Bayer array.

9. The medical observation system according to claim 1, wherein an image captured by at least one of the plurality of imaging elements has a resolution higher than or equal to 4K.

10. The medical observation system according to claim 1, wherein acquisition conditions of the plurality of images, from which the first composite image is generated, are different in at least one of an amount of light guided to the corresponding imaging elements, sensitivity of the imaging elements or a shutter speed of the imaging elements.

11. The medical observation system according to claim 10, wherein the incident light is split in such a manner that rays of light of different amounts are guided to two or more imaging elements that capture the images from which the first composite image is generated.

12. The medical observation system according to claim 10, wherein rays of light of different amounts are guided to each of two or more imaging elements that capture the images, from which the first composite image is generated, through control of a diaphragm provided as a preceding stage of each of the two or more imaging elements.

13. The medical observation system according to claim 1, wherein
of the plurality of imaging elements, two or more imaging elements that capture the images, from which the second composite image is generated, have mutually different optical distances from exit ends of the branching optical system.

14. The medical observation system according to claim 1, wherein the image processing device is further configured to generate a third composite image based on the first composite image and the second composite image.

15. The medical observation system according to claim 1, wherein
the medical observation device includes an endoscope unit including a lens barrel to be inserted into a body cavity of a subject, and
the endoscope unit is configured to capture an image of the subject acquired by the endoscope unit.

16. The medical observation system according to claim 1, wherein
the medical observation device further includes a microscope unit configured to acquire a magnified image of an imaging object, and
the microscope unit is further configured to capture an image of the imaging object acquired by the microscope unit.

17. A medical observation device, comprising:
a plurality of imaging elements; and
a branching optical system configured to split incident light into a plurality of rays of light, wherein
each of the plurality of rays of light split by the branching optical system is guided to at least one of the plurality of imaging elements,
two or more imaging elements of the plurality of imaging elements capture images having mutually different brightness,
two or more imaging elements of the plurality of imaging elements have different optical distances from the branching optical system,
the branching optical system includes a beam splitter configured to split second light into third light and fourth light,
the second light is obtained based on split of first light associated with a specific wavelength band from the incident light, and
of the plurality of imaging elements, a first imaging element through which the third light is guided and a second imaging element through which the fourth light is guided capture the images having mutually different brightness.

* * * * *